United States Patent [19]

Aig et al.

[11] Patent Number: 4,883,614
[45] Date of Patent: Nov. 28, 1989

[54] PHENYL SUBSTITUTED-2,4,6,8-NONATETRAENOIC ACID

[75] Inventors: Edward R. Aig, Fair Lawn; John W. Coffey; Allen J. Lovey, both of West Caldwell; Michael Rosenberger, Caldwell, all of N.J.

[73] Assignee: Hoffman-La Roche Inc., Nutley, N.J.

[21] Appl. No.: 922,621

[22] Filed: Oct. 24, 1986

Related U.S. Application Data

[63] Division of Ser. No. 746,812, June 20, 1985, now U.S. Pat. No. 4,648,996 which is a continuation-in-part of Ser. No. 635,100, Jul. 27, 1984.

[51] Int. Cl.$^4$ ............................................. C11C 1/00
[52] U.S. Cl. ..................................... 260/413; 260/408; 260/410.9 R
[58] Field of Search ................... 260/413, 408, 410.9 R

[56] References Cited

U.S. PATENT DOCUMENTS

| | | | |
|---|---|---|---|
| 3,984,400 | 10/1976 | Bollag et al. ................... | 260/413 X |
| 4,054,589 | 10/1977 | Bollag et al. ................... | 260/408 |
| 4,105,681 | 8/1978 | Bollag et al. ................... | 260/408 |
| 4,132,723 | 1/1979 | Pawson .............................. | 260/404 |
| 4,169,103 | 9/1979 | Haenni et al. ................... | 260/413 |
| 4,326,087 | 4/1982 | Fuchs ................................ | 568/631 |

FOREIGN PATENT DOCUMENTS

| | | |
|---|---|---|
| 0059365 | 9/1980 | European Pat. Off. . |
| 1101396 | 6/1965 | United Kingdom . |

OTHER PUBLICATIONS

Trown Cancer Research 40, 212 (1980).

*Primary Examiner*—Werren B. Lone
*Attorney, Agent, or Firm*—Jon S. Saxe; George M. Gould; William H. Epstein

[57] ABSTRACT

The compounds 9-phenyl-3,7-dimethyl-2,4,6,8 nonatetraenoic acids wherein the phenyl group is substituted with an alkyl, aminoalkyl, hydroxyalkyl, alkoxy, hydroxyalkylamino, and a hydroxy alkoxy group, and derivatives thereof which are used as disease modifying anti-rheumatic agents and as immunosuppressants.

23 Claims, 7 Drawing Sheets

LXX  LXI  XI-B

PHENYL SUBSTITUTED-2,4,6,8-NONATETRAENOIC ACID

This is a division of application Ser. No. 746,812, filed June 20, 1985, now U.S. Pat. No. 4,648,996, which in turn is a continuation in part of Ser. No. 635,100, filed July 24, 1984.

SUMMARY OF THE INVENTION

In accordance with this invention, it has been discovered that compounds of the formula:

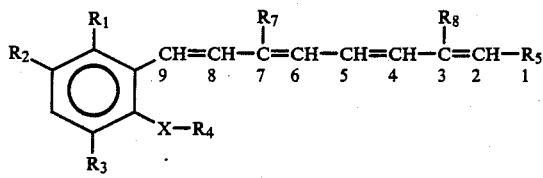

and compounds of the formula

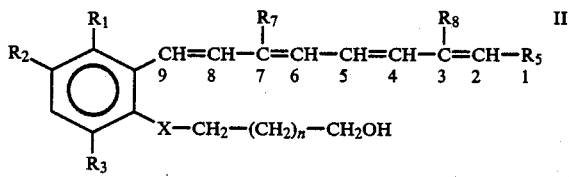

wherein n is an integer selected from 6 or 7; $R_1$ is hydrogen, loweralkyl, chlorine, fluorine or trifluoromethyl; $R_2$ is hydrogen, lower alkoxy, trifluoromethylloweralkoxy, hydroxy, lower alkyl, chlorine. trifluoromethyl, or fluorine; $R_3$ is hydrogen, loweralkyl, chlorine or fluorine; R is alkyl containing from 4 to 10 carbon atoms; X is

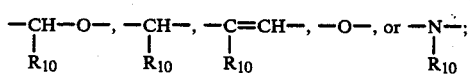

$R_5$ is

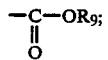

and $R_7$, $R_8$ $R_9$ and $R_{10}$ are individually lower alkyl or hydrogen; and salts thereof where $R_9$ is hydrogen, are useful in treating rheumatoid arthritis as well as related disorders and diseases resulting from immune hyperactivity.

In the past retinoids which have been active as disease modifiers for treating rheumatoid arthritis also tend to display the toxic symptoms of hypervitaminosis at dosages which show disease modifying effects. In accordance with this invention, the compounds of formula I and II possess this disease modifying effects while being relatively non-toxic. The compounds of formula I and II also act as immunosuppressant agents.

DETAILED DESCRIPTION

Figure 1:
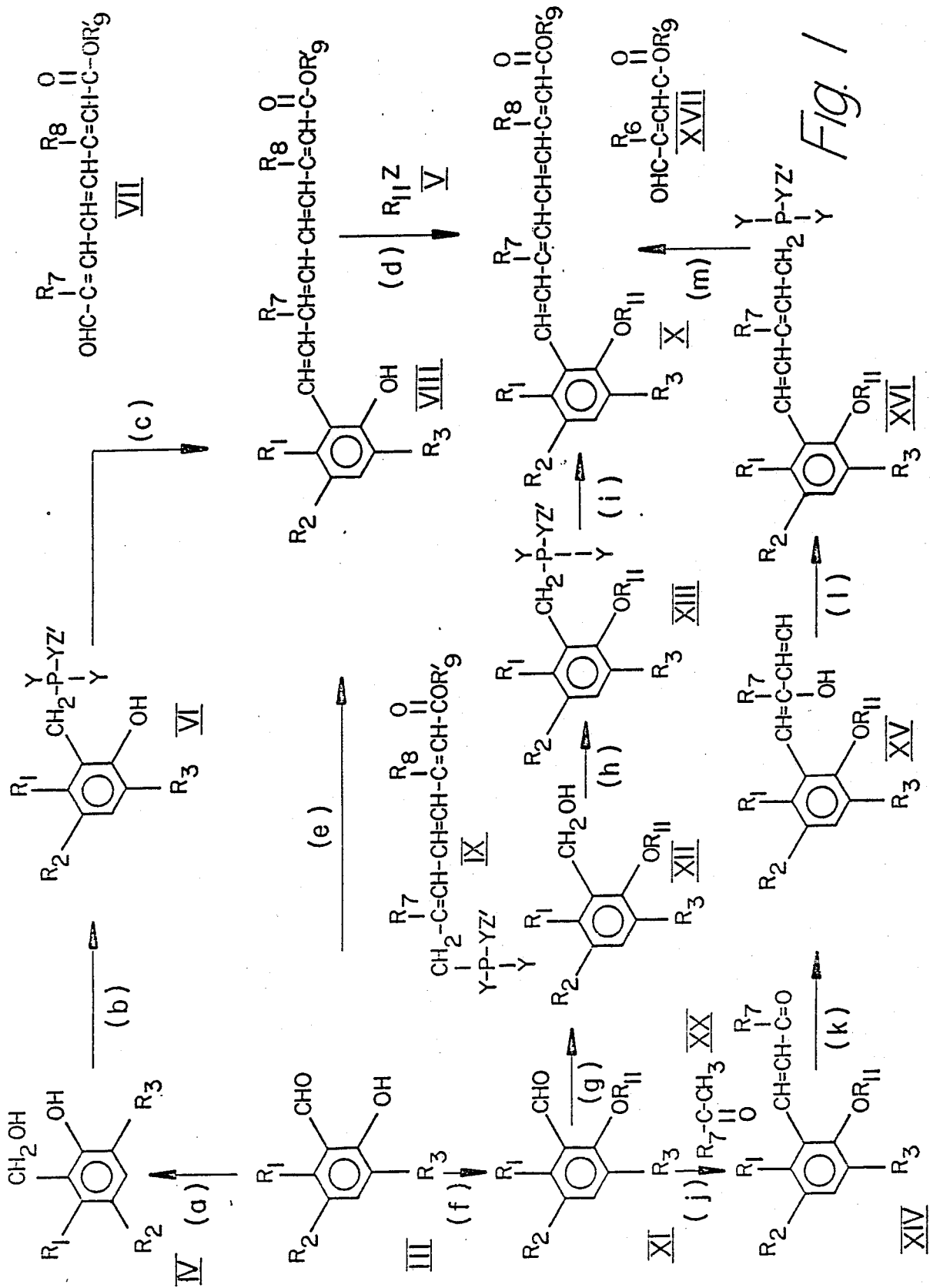

FIGS. 1, 2, 3, 4, 5, 6 and 7 represents schematic process steps for preparing the compounds of formula I and II above.

In the compounds of this invention the term "halogen" includes all four halogens, i.e. chlorine, bromine, iodine and fluorine with chlorine and bromine being preferred. The term "lower alkyl" as used herein designates both straight and branched chain lower alkyl group containing from 1 to 7 carbon atoms. Among the preferred lower alkyl groups are methyl, ethyl, isopropyl, n-butyl, etc., with methyl and ethyl being especially preferred. The term "lower alkoxy" designates lower alkoxy groups containing from 1 to 7 carbon atoms such as methoxy, ethoxy, isopropoxy, isobutyoxy, etc. The term trifluoromethyl lower alkoxy designates a trifluoromethyl substituted lower alkoxy substituent where lower alkoxy is defined as above. The term alkylidene designates a aliphatic saturated hydrocarbon group where the terminal carbon atoms is divalent.

The term "aryl" designates mononuclear aromatic hydrocarbon groups which can be unsubstituted or substituted in one or more positions with a lower alkyl groups, such as phenyl or tolyl, etc. and polynuclear aromatic groups which can be unsubstituted or substituted in one or more positions with a lower alkyl group and as napthyl, phenanthryl or anthryl the preferred aryl group is phenyl.

In one of the embodiments of the compounds of Formula I, $R_7$ and $R_8$ are lower alkyl preferably methyl and $R_4$ is preferably -(CH$_2$)y H with y being either 6 to 9 with 9 being especially preferred. In this embodiment of the invention, $R_1$, $R_2$ and $R_3$ are preferably hydrogen or $R_1$ and $R_3$ can be hydrogen and $R_2$ can be lower alkoxy such as methoxy or ethoxy. On the other hand in this embodiment $R_2$ and $R_3$ can be hydrogen with $R_1$ being chlorine or fluorine or $R_1$ and $R_2$ can be hydrogen with $R_3$ being chlorine or fluorine.

In one embodiment of the compound of formula II, $R_8$ and $R_7$ are lower alkyl, preferably methyl. In this embodiment of the compound of formula II, $R_1$, $R_2$ and $R_3$ are hydrogen, or $R_1$ is chlorine or fluorine with $R_2$ and $R_3$ being hydrogen. On the other hand in this embodiment of the compound of formula II. $R_1$ and $R_3$ are hydrogen and $R_2$ is lower alkoxy preferably methoxy or ethoxy. Also preferred are those compounds of this embodiment of the compound of formula II where $R_1$ and $R_2$ are hydrogen and $R_3$ is chlorine or fluorine.

Also included in this invention are salts of the compound of formulae I and II above with pharmaceutically acceptable, non-toxic, inorganic or organic bases, e.g. alkali metal and alkaline earth metal salts. Among the preferred salts are the sodium, potassium. magnesium or calcium salts, as well as salts with ammonia or suitable non-toxic amines, such as lower alkyl amines, for example triethylamine, hydroxy-lower alkylamines, for example 2-hydroxyethylamine, bis-(1-hydroxyethyl)amine or tris-(2-hydroxyethyl)-amine, cycloalkylamines, for example dicyclohexylamine, or benzylamines, for example N,N'-dibenzyl-ethylenediamine, and dibenzylamine. These salts can be prepared by treating the compounds of formulae I and II, where $R_9$ is hydrogen with inorganic or organic bases by conventional means well known in the art.

The compounds of formula I and II as well as salts thereof are effective as disease modifiers for treating rheumatoid arthritis as well as related disorders such as osteo-arthritis. The compounds of formula I and II also have activity as immunosuppressants.

The compounds of formulae I and II and salts thereof can be utilized to treat patients suffering from rheumatoid arthritis and related disorders. In such cases, the compounds modify the effects of these diseases by reducing destruction of the bone joints caused by this disease as well as reducing inflammation, heat and pain of the bone joints which results from rheumatoid arthritis and related disorders. The compounds of formulae I and II and salts thereof are also useful for treating diseases resulting from immune hyperactivity such as transplantation autoimmunity, autoimmune disease and graft versus host disease. The unexpected lack of toxicity of the compounds of this invention can be seen by the fact that the compound (all-E)-9-[2-(nonyloxy)-phenyl]-3,7-dimethyl-2,4-6,8-nonatetraenoic acid has a LD50 in mice of greater than 1,000 mg/kg both i.p. and p.o.

That the compounds of this invention are effective anti-arthritic agents can be seen from the results obtained when these compounds are administered to rats in accordance with the chronic adjuvant arthritis test system disclosed in Billingham and Davies "Handbook of Experimental Pharmacology" (editors J.R. Vane and S.H. Ferreira) Vol. 50/II, pg. 108-144, Springer-Verlag, Berlin, 1979).

In this procedure, adjuvant arthritis was induced by the subplantar injection on day o of 0.05 ml of adjuvant [a suspension of heat-killed, dessicated *Mycobacterium butyricum*, 0.5% (w/v), in heavy mineral oil containing 0.2% digitonin] into the right hind paw of male Charles River Lewis rats (120–140g) that were housed individually and given food and water ad lib. paw volumes (both hind paws) were measured immediately after injection of the adjuvant. paw Volumes were also measured, to follow the development of inflammation-induced swelling in the arthritic paws, at intervals of 3 to 7 days by immersion of the paw to the level of the lateral malleolus in a mercury plethysmograph.

Drugs were administered once a day (starting on the day of adjuvant injection) by incubation using Tween 80 (polyoxyethylene sorbitan mono-oleate) at a dose of 0.25 ml/100 g body Weight as the vehicle. Arthritic control rats received daily doses of the vehicle only. On day 23–25, the rats were sacrificed, plasma collected and plasma fibrinogen levels determined (ammonium sulfate turbidimetric method) as described by Exner et al., Amer. J. Clin Path, 71:521–527 (1979). Anti-inflammatory activity of the test drugs were determined by comparing the extent of paw swelling (paw volume on a particular day, i.e. day four to day twenty-five, minus the paw volume on day 0) in drug-treated arthritic rats with the extent of paw swelling in the vehicle-treated arthritic rats. Drug induced decreases in the level of plasma fibrinogen. an acute phase protein that is elevated in the plasma of rats with adjuvant-induced arthritis, were also used to quantitate the anti-inflammatory activity.

The results of various compounds of this invention when compared to Indomethacin and 13-cis-vitamin A acid are given in the following table (TABLE I).

TABLE I

| STRUCTURE | Oral Dose μMol/Kg | % Reduction in Paw Volume On day 23 | | Plasma fibrinogen % change (reduction) | Body Weight Gain (g) |
|---|---|---|---|---|---|
| | | Right | Left | | |
| Vehicle | — | — | — | — | 28–31 |
| Indomethacine | 3 | −66 | −67 | −30 | +46 |
| [structure with cyclohexenyl group and CO₂H] | 60 | −33 | −49 | −18 | −7 |
| [structure with OC₉H₁₉ phenyl and CO₂H] | 76 | −43 | −58 | −55 | +27 |
| [structure with MeO, OC₉H₁₉ phenyl and CO₂H] | 75 | −27 | −24 | −21 | +27 |
| [structure with NHC₈H₁₇ phenyl and CO₂Et] | 75 | −53 | −53 | | +24 |
| [structure with Cl, OC₉H₁₉ phenyl and CO₂H] | 75 | −29 | −32 | | +35 |

TABLE I-continued

| STRUCTURE | Oral Dose μMol/Kg | % Reduction in Paw Volume On day 23 | | Plasma fibrinogen % change (reduction) | Body Weight Gain (g) |
| --- | --- | --- | --- | --- | --- |
| | | Right | Left | | |
| 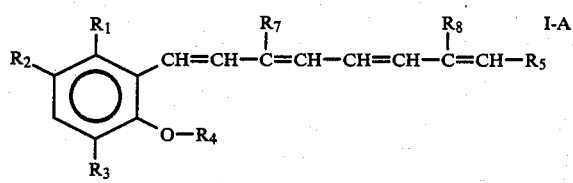 | 95 | −37 | −49 | −35 | +27 |
| 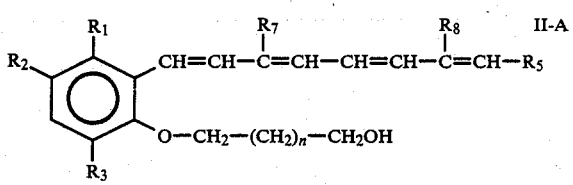 | 75 | −56 | −68 | −51 | +46 |

In the above Table I the percent reduction in paw volume demonstrates the effectiveness of the compounds of this invention to reduce swelling caused by adjuvant arthritis. As seen from the results in this Tablez, the compounds of this invention effectively reduce the swelling caused by the adjuvant. Furthermore the compounds of this invention were effective in reducing the plasma fibrinogen generally associated with rheumatoid arthritis. Furthermore as seen from the weight gain of the animals, the compounds of this invention at the dosage tested produced no substantial reduction in the weight gain of the animals. This indicates the lack of toxicity exhibited by the compounds of this invention.

The compounds of formulae I and II and their pharmaceutically acceptable salts can be used in a variety of pharmaceutical preparations. In these preparations, these compounds are administrable in the form of oral unit dosage forms such as tablets, pills, powders, capsules, as well as in such forms as injectables, solutions, suppositories, emulsions, dispersions, and in other suitable forms. The pharmaceutical preparations which contain the compounds of formulae I and II are conveniently formed by admixing with a non-toxic pharmaceutical organic carrier or a non-toxic pharmaceutical inorganic carrier. Typical of pharmaceutically acceptable carriers are, for example, water, gelatin, lactose, starches, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will, of course, vary with the particular novel compound employed, the chosen route of administration and the size of the recipient. The dosage administered is not subject to definite bounds but it will usually be in effective amounts of the pharmacologically function of the compounds of this invention. Representative of a typical method for administering the compounds of formulae I and II or their salts is by oral administration. By this route, the compounds of formulae I and II or their salts can be administered at a dosage of 0.5 mg/kg per day p.o. to 100 mg/kg per day p.o. Preferably these compounds can be administered daily to patients in unit oral dosage forms at daily dosages of from 1 to 30 mg/kg of body weight, with dosages of from 1 to 10 mg/kg being especially preferred.

The compound of formula I where X is —O— i.e. compounds of the formula:

$$\text{I-A}$$

wherein $R_1$, $R_2$, $R_3$, $R_4$, $R_5$, $R_7$ and $R_8$ are as above, and compounds of the formula II where X is —O— i.e. compounds of the formula $$\text{II-A}$$

wherein n, $R_1$, $R_2$ and $R_3$, $R_7$, and $R_8$ are as above, can be prepared from compounds of the formula

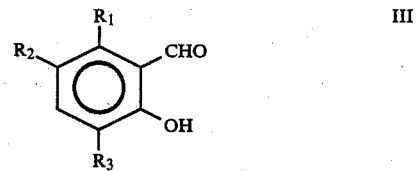

wherein $R_1$, $R_2$ and $R_3$ are as above, via the reaction scheme in FIG. 1.

In the reaction scheme of FIG. 1, $R_{11}$ is both —CH$_2$—(CH$_2$)n—CH$_2$OH and $R_4$. Also in this reaction Scheme n, $R_1$, $R_2$, $R_3$, $R_7$ and $R_8$ are as above and $R'_9$ is lower alkyl, Z is a leaving group; Y is aryl preferably phenyl; Z' is halo.

The compound of formula III is converted to the compound of formula IV via reaction step (a) by reducing the aldehyde group to the alcohol. This reaction is carried out utilizing a conventional reducing agent which converts aldehydes to alcohols. Any conventional reducing agent for this purpose can be utilized in the reaction of step (a). In carrying out this reaction it is generally preferred to utilize an alkali metal borohydride such as sodium borohydride as the reducing agent. Any of the conditions conventional in such reduction reactions can be utilized to carry out the reaction of step (a). If $R_2$ is hydroxy it is generally preferred to protect the hydroxy designated by $R_2$ during the reduction of the compound of formula III and its subsequent conversion to the compound of formula II-A. Any conventional hydrolizable hydroxy protecting group such as a lower alkanoyl group may be utilized to protect the hydroxy group when $R_2$ is hydroxy. This ester protecting group can be cleaved by conventional ester hydrolysis after the formation of the Wittig salts of formulae XIII and XVI or after the formation of the ether of formula X.

The compound of formula IV is converted to the compound of formula VI via reaction step (b) by treating the compound of formula IV with a triarylphosphine hydrohalide. In this manner the phosphonium salt of formula VI is produced. Any conventional method of reacting an allylic alcohol with a triarylphosphine hydrohalide can be used to carry out this reaction. The phosphonium salt of formula VI is reacted via a Wittig reaction with the compound of formula VII in step (c) to form the compound of formula VIII. Any of the conditions conventionally used in Wittig reactions can be utilized to carry out the reaction of step (c).

On the other hand the compound of formula III may be directly converted to the compound of formula VIII via the reaction with the phosphonium salt of the compound of formula IX as in reaction step (e). The reaction of the phosphonium salt of formula IX with the compound of formula III to produce the compound of formula VIII is carried out utilizing the same conditions as described in connection with reaction step (c).

The compound of formula VIII is converted to the compound of formula X by etherifying or alkylating the compound of formula VIII with a compound of formula V as in reaction step (d). In the compound of formula V, Z can be any conventional leaving group such as mesyloxy, tosyloxy or a halide. Any conventional method of etherification of a hydroxy group though reaction with a halide or a leaving group can be utilized to carry out the reaction of step (d).

In accordance with another embodiment of this invention the compound of formula X, where when $R_2$ is hydroxy, the hydroxy group is protected via a hydrolizable ester, can be produced from the compound of the formula III by alkylation or etherification of the compound of formula III with the compound of formula V to produce the compound of XI. This reaction is carried by alkylating the compound of formula III with the compound of formula V as in step (d). In the reaction of steps (f) and (d) where $R_{11}$ is a hydroxy alkyl group, the hydroxy contained in $R_{11}$ need not be protected. This is true since under the conditions used in this reaction step, the compound of formula V will react with either the compound of formula III or the compound of formula VIII to produce the compound of formula XI or the compound of formula X without the necessity for protecting the hydroxy group contained on the alkyl chain. Alkylation or etherification will occur directly with the phenyl hydroxy moiety on either the compound of formula III or the compound of formula VIII and there will be little, if any reaction with the hydroxy group contained on the alkyl chain designated by $R_{11}$. The compound of formula XI is converted to the compound of formula XII, via reaction step (g) by reduction. The same conditions described in connection with reaction step (a) can be utilized to convert the compound of formula XI to the compound of formula XII.

The compound of formula XII is converted, via reaction step (h), to the compound of formula XIII by treating the compound of formula XII with a triarylphosphine hydrohalide in the manner described hereinbefore in connection with step (b). The compound of formula XIII is converted to the compound of formula X by reacting the compound of formula XIII with the compound of formula VII via reaction step (i). This reaction step is carried out in the same manner as described eereinbefore in connection with reaction step (c).

In accordance with another embodiment of this invention the compound of formula X is produced by first converting the compound of formula XI to the compound of formula XIV. The compound of formula XI is converted to the compound of formula XIV by aldol condensation with the compound of formula XX. Any conventional method of aldol condensation can be utilized to react the compound of formula XI with the compound of formula XX to form the compound of formula XIV. In the next step the compound of formula XIV is condensed via either a Grignard reaction with vinyl magnesium halide or a lithium condensation reaction with vinyl lithium to produce the compound of formula XV. The reaction of step (k) can be carried out by utilizing any of the conditions conventional in lithium condensations or Grignard condensation reactions. The compound of formula XV is converted to the compound of formula XVI by reacting the compound of formula XV with a triarylphosphine hydrohalide in the manner described hereinbefore in connection with the reaction of step (b). The compound of formula XVI is thereafter converted to the compound of formula X, via reaction step (m), by reaction with the compound of formula XVII. The reaction of step (m) is carried out utilizing a standard Wittig reaction as described in connection with the reaction of step (c). The compound of formula XVI by the reaction with the compound of formula XVII produces the compound of formula X. The compound of formula X is the compound of formula I-A and II-A where $R_5$ is an esterified carboxy group. The compound of formula X can be converted to the free acid i.e. the compound of formula I-A and II-A where $R_5$ is COOH by ester hydrolysis. Any conventional method of ester hydrolysis will produce the compound of the formula I-A and II-A and where $R_5$ is COOH.

the compound of formula I where X is

i.e. compounds of the formula

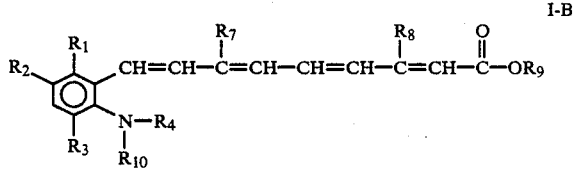

wherein $R_1$, $R_2$, $R_3$, $R_4$, $R_7$, $R_8$, $R_9$ and $R_{10}$, are as above, and compounds of the formula II where X is i.e. compounds of the formula:

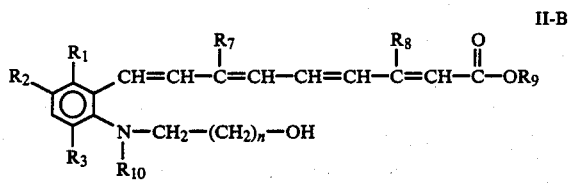

wherein n, $r_1$, $R_2$, $R_3$, $R_8$, $R_7$, $R_9$ and $R_{10}$ are as above; are prepared from the compound of the formula

Figure 2:
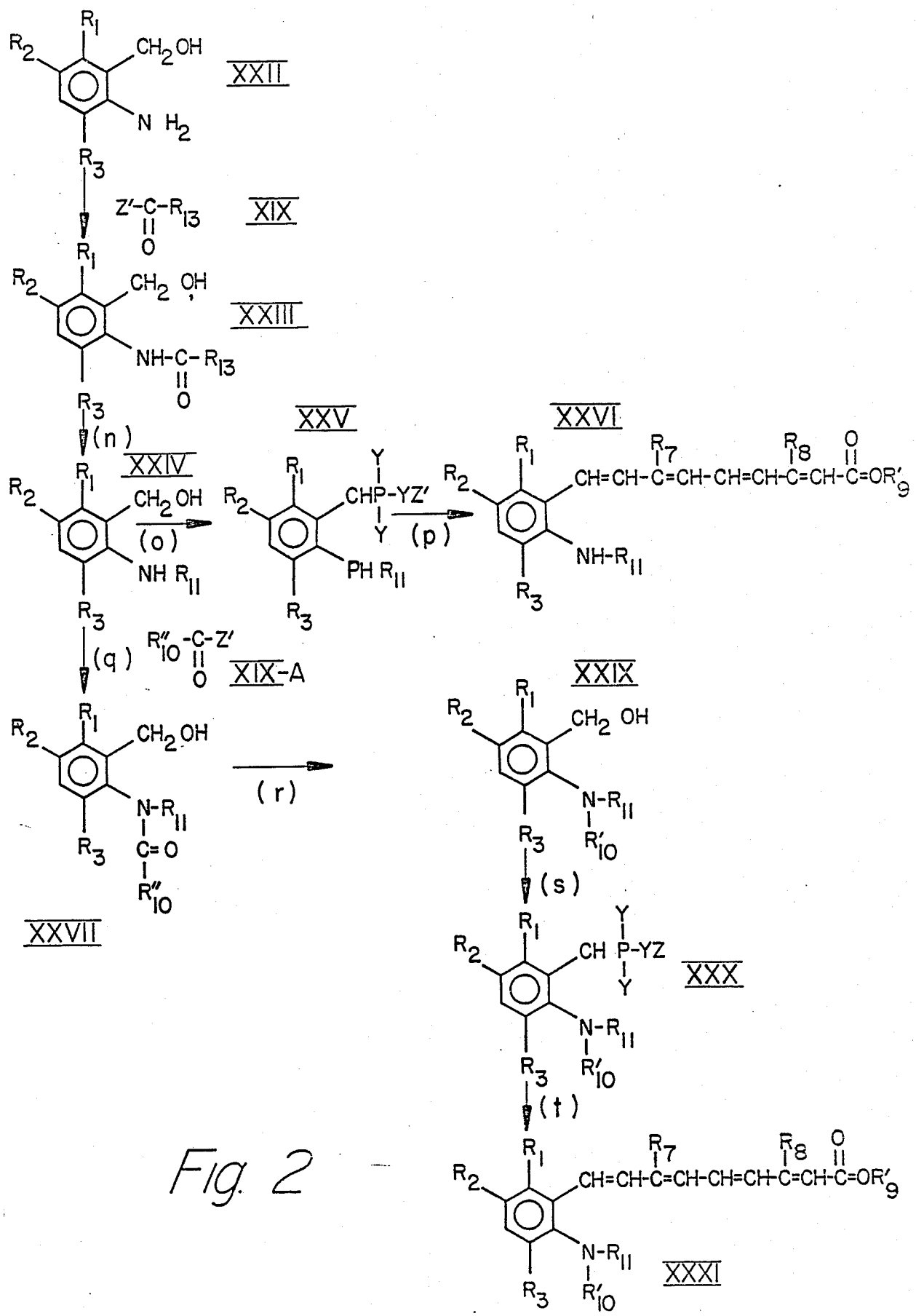

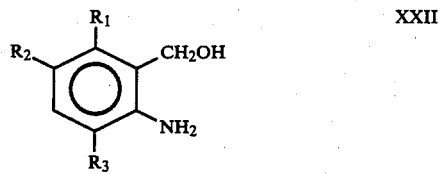

wherein $R_1$, $R_2$ and $R_3$ are as above via the reaction scheme in FIG. 2.

In FIG. 2, $R_1$, $R_2$, $R_3$, $R_7$, $R_8$, $R_9'$, $R_{11}$, $Z'$ and Y are as above. In FIG. 2, $R_{13}$ is the same as $R_4$ however it is an alkyl group with one less carbon than the alkyl group contained by $R_4$. Therefore $R_{13}$ is an alkyl group containing from 3 to 9 carbon atoms. On the other hand, $R_{13}$ can also be $-CH_2(CH_2)_mCH_2OH$ where m is a number one less than n. Therefore $R_{13}$ is $-CH_2-(CH_2)_m-CH_2OH$ where m is an integer of from 5 to 6. In FIG. 2, $R_{10}$ is hydrogen or lower alkyl containing from 1 to 7 carbon atoms and $R_{10}'$ is a lower alkyl group containing from 1 to 7 carbon atoms. In this embodiment $R_{10}''$ is a lower alkyl group having one carbon atom less than the alkyl group designated by $R_{10}'$.

In FIG. 2 the compound of formula XXII is reacted with acid chloride of formula XIX where Z' is halogen to produce the compound of formula XXIII which is later converted either to the compound of formula XXVI or the compound of XXXI. Where $R_{13}$ in the compound of formula XIX is $-CH_2-(CH_2)_mCH_2OH$ where m is an integer of from 5 to 6 carbon atoms, the presence of the hydroxy group on the substituent of $R_{13}$ will not effect the reaction to produce the compound of formula XXVI or the compound of formula XXXI. It has been found that this hydroxy group remains unaffected throughout the series of reactions set forth in FIG. 2.

On the other hand this hydroxy group can be protected by means of forming a hydrolyzable ether functional group which protects the hydroxy group throughout these reactions. Any conventional ether protecting group can be utilized to protect the hydroxy group throughout these reactions. Among the preferred ether protecting groups, are included: tetrahydropyranyloxy, t-butoxy, triloweralkylsilyloxy. i.e. trimethylsilyloxy, etc. Any conventional ether protecting group can be utilized to protect the terminal hydroxy group which may be present as $R_{13}$. On the other hand, the reactions set forth in FIG. 2 can be carried out without any protection of the terminal hydroxy group.

In the first step of the reaction, the compound of formula XXII is reacted with the compound of formula XIX to produce the compound of formula XXIII. Any conventional method of condensing an amine with an acid halide can be utilized to carry out this reaction. In the next step the compound of formula XXIII is converted to the compound of formula XXIV, via reaction step (n), by treating the compound of formula XXIII with a reducing agent. Any conventional alkali metal aluminum hydride reducing agent can be utilized to carry out this reaction with the preferred reducing agent being lithium aluminum hydride. Any of the conditions conventional in reducing with an alkali metal aluminum hydride reducing agent can be utilized to carry out this reaction.

The compound of formula XXIV can be converted to the compound of formula XXVI via the intermediate XXV. In the first step of this procedure, step (o), the compound of formula XXIV is converted into the phosphonium salt of formula XXV by reaction with a triarylphosphine hydrohalide as described hereinbefore in connection with the reaction of step (b). The compound of formula XXV is converted to the compound of formula XXVI via reaction step (p), by reaction with the aldehyde of formula VII. (See FIG. 1). The reaction of step (p) to produce the compound of formula XXVI is carried by a Wittig reaction in the same manner as described in reaction step (c) hereinbefore. The compound of formula XXVI where $R_9$ is lower alkyl can, if desired, be converted into the free acid by conventional basic hydrolysis. Any conventional method of basic hydrolysis to hydrolize esters can be utilized to convert the compound of formula XXVI to the free acid. On the other hand, the compound of formula XXVI where $R_{11}$ contains a terminal hydroxy group etherified with a conventional ether protecting group can be converted into the free alcohol by acid hydrolysis. Any of the conventional methods of hydrolyzing ethers can be utilized to carry out this reaction. The ether hydrolysis of the compound of formula XXVI can be carried out either before or after the acid hydrolysis used to hydrolize the ester protecting $R_9'$. On the other hand if $R_{11}$ in the compound of formula X in FIG. 1 contains an etherified hydroxy group, the compound of formula X can be hydrolyzed in the same manner as is the compound of formula XXVI.

On the other hand, the compound of formula XXIV can be converted to the tertiary amine compound of formula XXXI. In this reaction, the compound of formula XXIV is reacted, via reaction step (q), with the acid halide of formula XIX-A, to produce the compound of formula XXVII in the same manner described hereinbefore in connection with the reaction to convert the compound of formula XXII to the compound of formula XXIII.

The compound of formula XXVII is converted to the formula XXIX, via reaction step (r), by treating the compound of formula XXVII with a lithium aluminum hydride reducing agent as described in connection with reaction of step (n).

In the next step of this reaction scheme, the compound of formula XXIX is converted to the compound of formula XXX, via reaction step (s), by treating with a triarylphosphine hydrohalide. This reaction is carried out in the same manner as described in connection with reaction step (b) described hereinbefore. The compound of formula XXX is converted to the compound of formula XXXI, via reaction step (t), by reaction with the compound of formula VII (FIG. 1). In carrying out the reaction of step (t) a Wittig reaction is utilized. The reaction of step (t) can be carried out in the same manner as described hereinbefore in connection with the reaction of step (c). The compound of formula XXXI where R$_9$' is a lower alkyl group can be converted, if desired, to the corresponding compound of the formula XXXI containing the free acid group by basic hydrolysis. On the other hand, if R$_{11}$ contains a terminal hydroxy group protected through the formation of a hydrolizable ether, the compound of formula XXXI can be converted to the corresponding compound where R$_{11}$ is a free hydroxy group by conventional ether hydrolysis. This ether hydrolysis can be carried out before or after hydrolysis of the ester group denoted by R$_9$'.

In the reaction scheme of FIG. 2, when R$_2$ is hydroxy, it is preferred that this hydroxy group be protected via the formation of an ester protecting group. The ester protecting group can be removed after the formation of the Wittig salts of formula XXX.

The compounds of formula I and II where X is

where R$_{10}$ is hydrogen or lower alkyl have the formula:

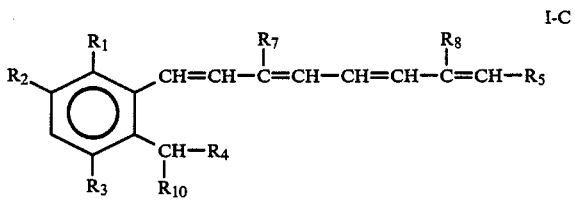

and

Figure 3:
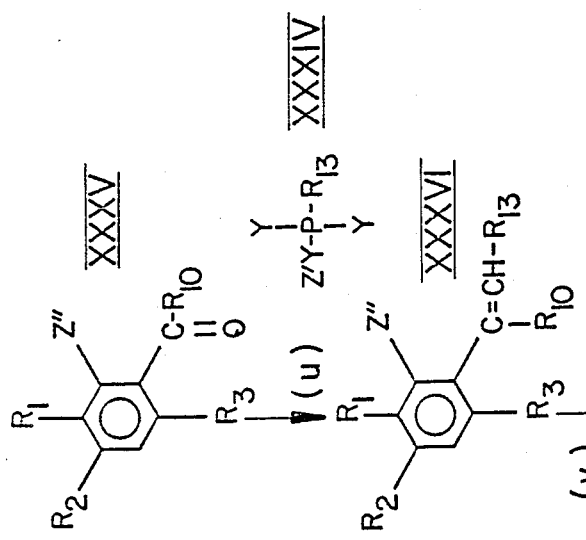
Figure 3:
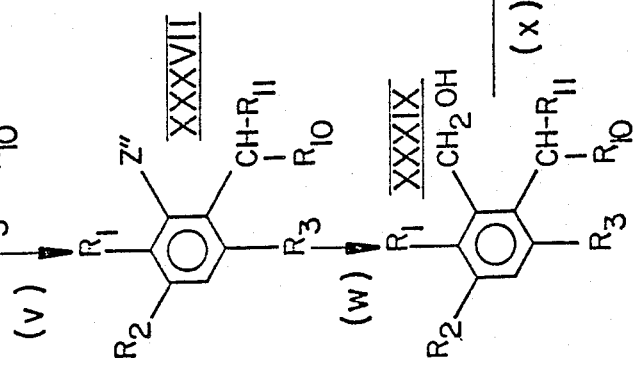

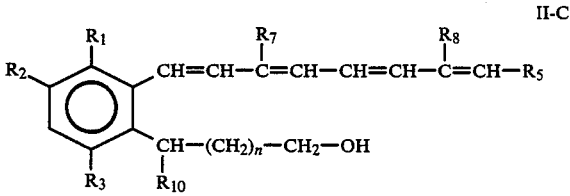

wherein n, R$_1$, R$_2$, R$_3$, R$_4$, R$_5$, R$_7$, R$_8$ and R$_{10}$, are as above are prepared from a compound of the formula:

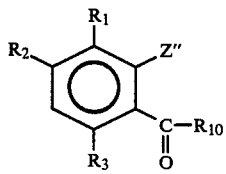

wherein Z" is ether bromo or iodo; R$_1$, R$_2$, and R$_3$ are as above; and R$_{10}$ is hydrogen or lower alkyl as set forth in FIG. 3. In FIG. 3, R$_1$, R$_2$, R$_3$, R$_7$, R$_8$, R'$_9$, R$_{10}$, R$_{11}$, R$_{13}$, Y, Z', and Z" are as above.

In FIG. 3, the compound of formula XXXV is first reacted with the compound of formula XXXIV via reaction step (u) to produce the compound of formula XXXVI. This reaction is carried out via a Wittig reaction. In the compound of formula XXXVI R$_{13}$ can be, if desired, —CH$_2$—(CH$_2$)$_m$ - OH where the free hydroxy group can, if desired, be protected through the formation of any of the aforementioned conventional ether groups. On the other hand it has been found that this OH group can be a free hydroxy group and need not be protected by means of an ether protecting group. In carrying out the reactions of FIG. 3 this free hydroxy group is not affected by the reactions which convert the compound of formula XXXVI to the compound of formula XXXXI. However for best yields it is generally preferred to protect this hydroxy group via the formation of a hydrolizable ether.

The reaction of step (u) is carried out via a Wittig reaction between the compounds of formula XXXV and the compound of formula XXXIV utilizing the same reaction conditions as described hereinbelow in connection with reaction step (c).

The compound of formula XXXVI can be converted to the compound of formula XXXVII via a reaction step (v) by hydrogenation. Any conventional method of hydrogenation can be utilized to carry out this reaction. Among the conventional methods of hydrogenation are included treating the compound of formula XXXVI, in an inert organic solvent medium, with hydrogen gas in the presence of a catalyst. Any conventional hydrogenation catalyst can be utilized in carrying out this reaction. Among the preferred catalysts are included palladium. In carrying out this reaction any conventional inert organic solvent can be utilized. Furthermore, any of the conditions conventional in catalytic hydrogenation can be utilized in reaction step (v).

In the next step of this reaction, the compound of formula XXXVII is converted to the compound of formula XXXIX via reaction step (w), by treating compound of formula XXXVII with formaldehyde or a formaldehyde liberating compound. In carrying out this reaction the compound of formula XXXVII is first metalated with an alkali metal alkyl e.g. n-butyllithium. Generally this reaction is carried out in an inert organic solvent such as an ether solvent. Among the preferred solvents are diethyl ether and tetrahydrofuran. In carrying out this reaction temperature and pressure are not critical. This reaction can be carried out at room temperature and atmospheric pressure. If desired, higher and lower temperatures can be utilized. After treating the compound of formula XXXVIII with an alkali metal alkyl, formaldehyde or a formaldehyde liberating compound is added to the reaction medium. Any conventional compound capable of liberating formaldehyde such as paraformaldehyde can be utilized in carrying out this reaction. This reaction is carried out in the same reaction medium and utilizing the same conditions as the metalation of the compound of formula XXXVIII was carried out.

The compound of formula XXXIX is converted to the compound of formula XXXX, via reaction step (x), by treating the compound of formula XXXIX with triarylphosphine hydrohalide. This reaction is carried out in the same manner as described in connection with reaction step (b) as described hereinbefore. The compound of formula XXXX is converted, via reaction step (y), to the compound of formula XXXXI by reaction with the compound of formula VII. (See FIG. 1). This reaction of step (y) is carried out via a Wittig reaction utilizing the same conditions described in connection with reaction step (c). The compound of formula XXXXI may be converted to corresponding compound containing the free carboxyl group instead of R$_9$'. This reaction is carried out by conventional ester hydrolysis in the manner hereinbefore described. Any conventional method of ester hydrolysis can be utilized. If R$_{11}$ contains terminal hydroxy group protected through the use of an ether protecting group. this ether group can be hydrolized to yield the free hydroxy group by conventional ether hydrolysis such as by utilizing an aqueous inorganic acid. Any conventional method of ether hydrolysis can be utilized. The protected ether hydroxy group can be hydrolized either prior to or after hydrolysis of the ester group to form the free acid of the compound of formula XXXXI.

If it is desired to produce compounds of the formulae I and I-A where Y is

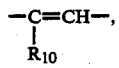

the compound of formula XXXV in FIG. 3 is reacted, via reaction step (u), with the compound of formula XXXIV where $R_{13}$ is $R_{11}$ to produce the compound of formula XXXVI where $R_{13}$ is $R_{11}$. This compound of formula XXXVI where $R_{11}$ is $R_{13}$ is then subjected to the same series of reactions as the compound of formula XXXVII, i.e. the reaction steps (w), (x) and (y), to produce the compounds of formulae I and I-A where X is

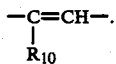

In the reaction scheme in FIG. 3 where $R_2$ in the compound of formula XXXV is a hydroxy group, it is preferred to protect this hydroxy group via esterification with a lower alkanoic acid. This ester protecting group can be cleaved after formation of the Wittig salt of formula XXXX.

The compound of formula I and II where X is

has the formula

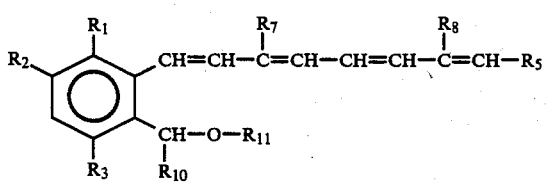

wherein $R_1$, $R_2$, $R_3$, $R_5$, $R_7$, $R_8$, $R_{10}$ and $R_{11}$ are as above can be prepared from a compound of the formula

Figure 4:
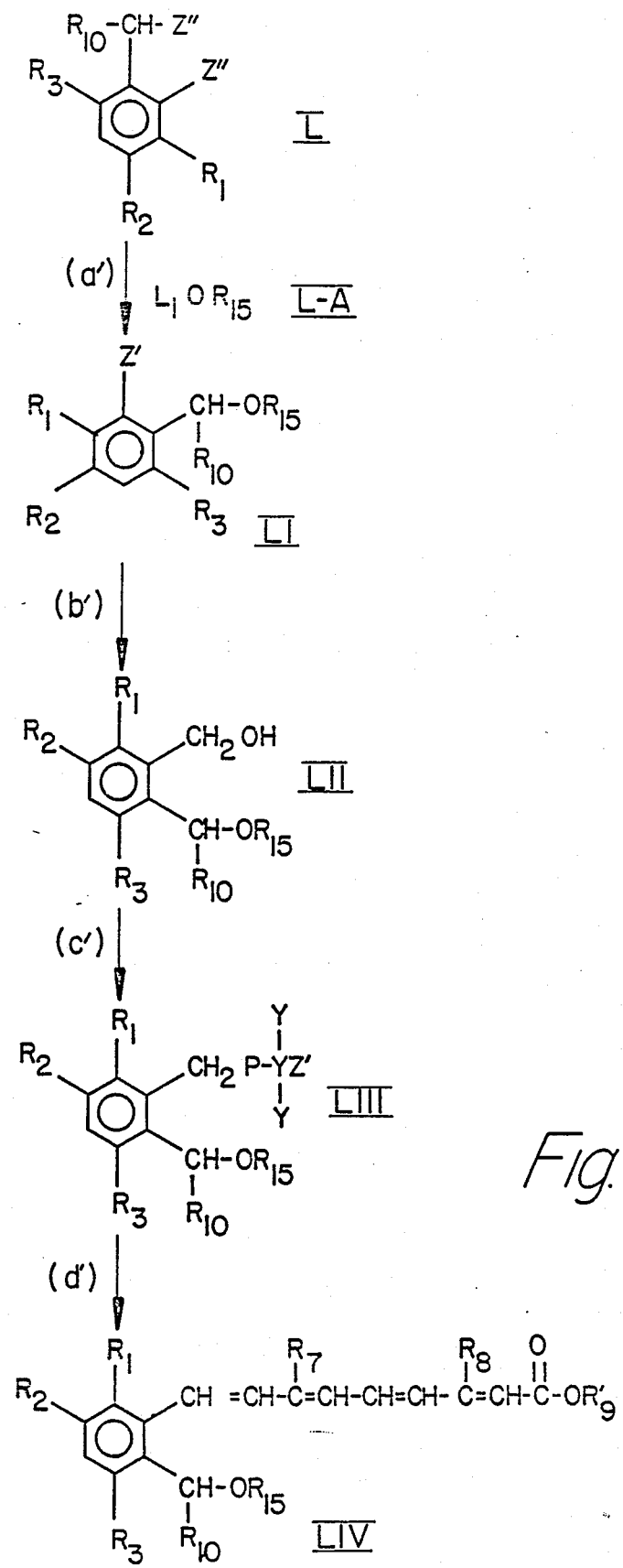

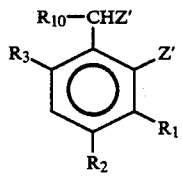   L wherein $R_1$, $R_2$, $R_3$ and Z" as above by the reaction scheme of FIG. 4. In FIG. 4, $R_1$, $R_2$, $R_3$, $R_7$, $R_8$, $R_{10}$, $R_9'$, Y and Z"are as above and $R_{15}$ is $R_4$ or —CH$_2$-(CH$_2$)$_n$ —CH$_2$OR$_{17}$ wherein $R_{17}$ taken together with its attached oxygen atom forms a hydrolizable ether group such as tetrahydropyranyl as well as the ether groups mentioned hereinbefore and n is as above.

The compound of formula L is converted to the compound of formula LI by reaction with the alkali metal alkoxide of formula L-A. This reaction is carried out by reacting the compound of formula L with the compound of formula L-A utilizing the conditions conventional in reacting an alkali metal alkoxide with a halide.

In the step, the compound of formula LI is converted to the compound of formula LII by first treating the compound of formula LI with an alkyl lithium such as n-butyl lithium to metalate the compound of formula LI. The metalated compound of formula LI is thereafter reacted with formaldehyde or a formaldehyde liberating compound. In converting the compound of formula LI to the compound of formula LII, the same reaction conditions as described in connection with reaction step (w) are used in this conversion. The compound of formula LII is converted to the phosphonium salt of formula LIII treating the compound of formula LII with a triarylphosphine hydrohalide in the manner set forth in reaction step (b) above. The phosphonium salt of formula LIII is reacted via a Wittig reaction with the compound of formula VII (see FIG. 1) to form a compound of formula LIV. This reaction to form the compound of formula LIV is carried out in the same manner as described in connection with step (c) hereinbefore.

When $R_4$ in the compound of formula LIV contains the protected hydroxy substituent i.e., where $R_{17}$ taken together with its attached oxygen and forms the hydrolizable ether group. $R_{17}$ can be hydrolized to form the free hydroxy compound by conventional methods for hydrolizing easily removable ether groups. Any conventional method for hydrolizing ether protecting groups can be utilized. The conditions conventional for hydrolizing ether protecting groups will not affect the other ether group contained within the compound of formula LIV. The compound of formula LIV can be converted to the free acid by conventional ester hydrolysis.

If $R_2$ in the compounds of formulae L, LI, LII and LIII is hydroxy, it is preferable that the hydroxy group be protected via a hydrolyzable ester group such as lower alkanoyloxy. The hydrolyzable ester protecting group can be cleaved after forming the Wittig salt of formula LIII.

If desired, the double bonds within the compound of formula I and II at positions 2-3, 4-5,6-7 and 8-9 can be either in the cis or, trans configuration. On the other hand, these compounds can be a mixture of the various cis and trans isomers. In the compound of formula VII, the double bonds contained therein can be either in the cis or trans configuration depending upon the desired stereo configuration of the double bonds within the compounds of formula I and II. The Wittig reaction carried out in producing the compounds of formula I and II suc as in steps (c), (e), (i), etc. Produces the double bond at the 8-9 position as a mixture of the 8-9 cis and trans isomers. These cis and trans isomers can be separated by conventional means such as fractional crystallization, etc.

In addition, where the compounds of formula I and/or II have a double bond in the trans configuration at the 2-3 position, this isomer can be converted to the corresponding cis double bond with conventional methods of isomerization known in the art. Among these procedures are included treating the compound of either formula I or II with iodine in an inert organic solvent. Isomerization with iodine produces the compound of formula I with a 2-3 double bond in the cis position.

The compounds of formula I and II include all of its geometric isomers including mixtures of these geometric isomers.

The compound of formula XI where $R_1$ is fluoro is a new compound and can be prepared from a compound of the formula

Figure 5:
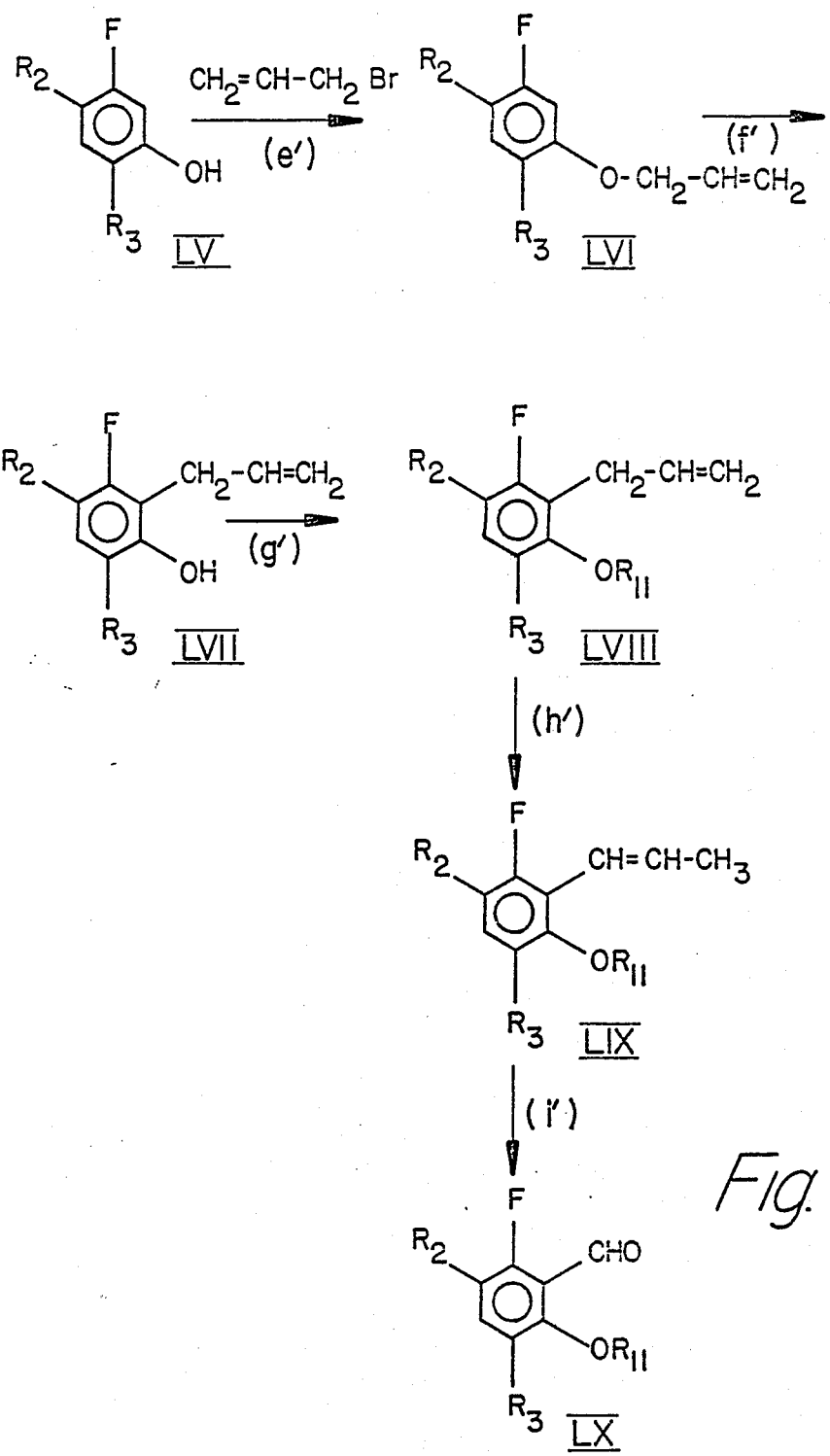

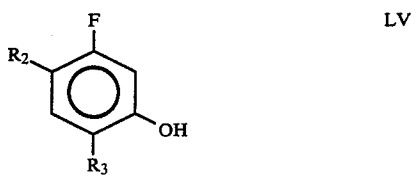

where $R_2$ and $R_3$ are above via the reaction scheme given of FIG. 5. In FIG. 5, $R_2$, $R_3$ and $R_{11}$ are as above.

In FIG. 5, the compound of formula LV is alkylated by reaction with an allyl bromide. If the compound where $R_2$ is hydroxy is desired, the compound of formula LV where the hydroxy group designated by $R_2$ is protected by esterification is used as the starting material, i.e. the compound of formula LV where $R_2$ is a protected hyroxy group. Any conventional method of alkylating a hydroxy group with an allyl bromide can be utilized to carry out the reaction of converting the compound of LV to the compound of formula LVI. The compound of formula LVI is rearranged to the compound of formula LVII by heating the compound of formula LVI to a temperature from 190 degrees to 230 degrees centigrade. This rearrangement can take place without the use of any solvent or in the presence of a high boiling hydrocarbon solvent. If $R_3$ is hydrogen, the compound of formula LVII is formed as a mixture with the isomer of the compound of formula LVII where the allyl group is para to the fluorine substituent on the benzyl ring. This isomer can be separated or utilized in the subseguent reactions and separated from the reaction mixture at a later stage.

The compound of forula LVII is thereafter converted to the compound of formula LVIII by reaction with the compound of formula V (FIG. 1) as set forth in reaction step (d) hereinbefore. In the next step of this reaction scheme, the compound of formula LVIII is converted to the compound of formula LIX by isomerization with a strong base such as an alkali metal alkoxide in the presence of an inert organic solvent preferably potassium tertiary butoxide in dimethyl sulfoxide. The compound of formula LIX is converted to the compound of formula LX by treating the compound of formula LIX with ozone gas. In carrying out this reaction, temperatures of from minus 70 degrees centigrade to minus 20 degrees centigrade are utilized. Furthermore this reaction is carried out in an inert organic solvent. Any conventional inert organic solvent can be utilized, preferably halogenated hydrocarbons such as methylene chloride.

Figure 6:
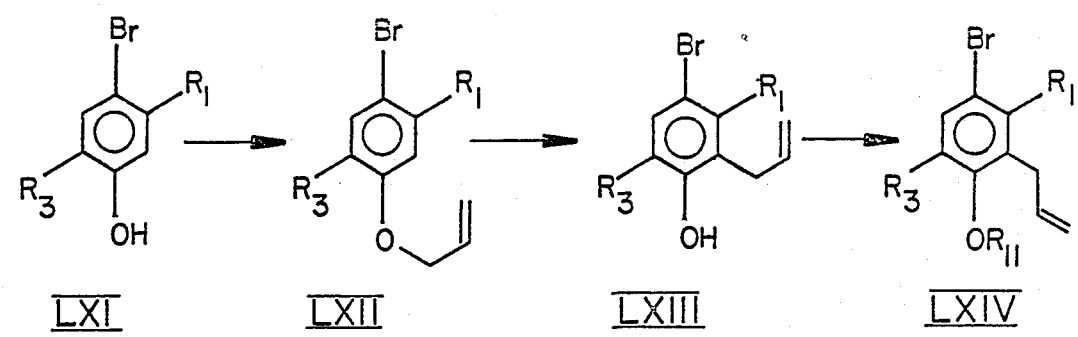
Figure 6:
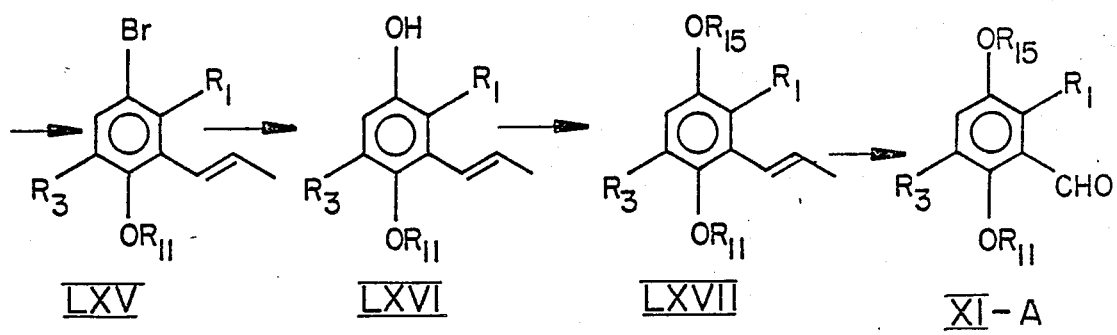

A compound of formula LX is the compound of formula XI wherein $R_1$ is fluoro. This compound can be converted to the compound of formula X in accordance with the reaction scheme set forth in FIG. 1.

Where $R_2$ is hydroxy in the compound of formula III there are two hydroxy groups. Therefore, it is generally preferred to prepare the compound of formula XI where $R_2$ is a protected hydroxy group from a compound of the formula LXI as shown in FIG. 6. In this manner, compounds of formula I-A and II-A can be prepared where $R_2$ is hydroxy and $R_3$ and $R_{11}$ are as above. In FIG. 6, $R_1$ and $R_{15}$ taken with its attached oxygen atom, is hydroxy protected by a conventional hydrolyzable protecting group preferably a lower alkanoyl.

In FIG. 6, the compound of Formula LXI is converted to the compound of formula LXII utilizing the same reaction as described in connection with the conversion of a compound of Formula LV to a compound of the Formula LVI. (See FIG. 5) The compound of Formula LXII is next converted to a compound of Formula LXIII by utilizing the same procedure described in connection with the conversion of the compound of Formula LVI to LVII. In the next steps the compound of Formula LXIII is converted to the compound LXIV by the same procedure described in connection with step (g') in FIG. 5 and then to the compound of Formula LXV by the procedure described in connection with step (h') in FIG. 5. The conversion of bromobenzene compound of Formula LXV to the phenol compound of Formula LXVI takes place by procedures well known in the art such as disclosed by Kidwell and Darling, Tetrhhedron Letters, (1966) pgs. 531–535.

In the next step of preparing the intermediate of formula XI where $R_2$ is a protected hydroxy group, i.e. the compound of Formula XI-A, the hydroxy group is protected on the compound of formula LXVI through esterification with any conventional hydrolyzable ester group to form the compound of Formula LXVII where $R_{15}$ taken together is attached oxygen forms a hydrolyzable ester group. Any conventional method of esterifying a hydroxy groups with an organic acid such as a lower alkanoic acid containing from 1 to 7 carbon atoms can be used to prepare the compound of Formula LXVII. The compound of Formula XI-A is formed from the compound of Formula LXVII by the reaction described hereinbefore with respect to the conversion of a compound of the Formula LIX to LX (See FIG. 5).

Figure 7:
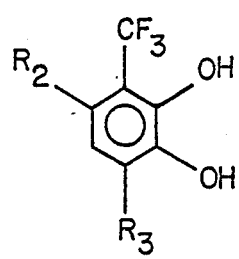
Figure 7:
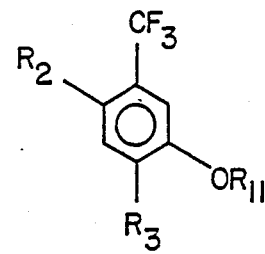
Figure 7:
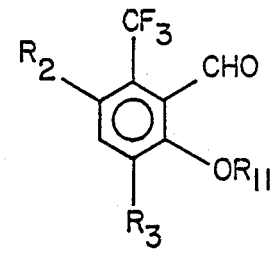

In carrying out the conversion of a compound of Formula XI-A, to a compound of Formula XVII, as in FIG. 1, it is generally preferred to hydrolyze the ester substituent which forms $R_2$ after the formation of the Wittig salt of Formula XIII or Formula XVI In accordance with another embodiment of this invention the compound of formula XI where $R_1$ is $CF_3$ (the compound of formula XI-B) can be formed by the reaction outlined in FIG. 7 from a compound of Formula LXX. In the first step of this reaction the compound of Formula LXX is converted to a compound of Formula LXXI utilizing the same procedure described hereinbefore in connection with the reaction, via step (d) where the compound of Formula VIII is reacted with a compound of the Formula V to produce a compound of the Formula X. In this reaction where $R_2$ is OH, alkylation occurs very slowly on the hydroxy group ortho to the $CF_3$ group. Therefore, protection of this group may not be necessary since alkylation proceeds preferably with the meta hydroxy group. Any mixtures of alkylated products obtained from this reaction can be separated by conventional separation procedures. The compound of formula LXXI is converted to the compound of formula XII-B by conventional procedures of formylating a benzene ring such as by treatment with an alkyl lithium and dimethylformamide.

The following examples are illustrative but limitative of the invention. In the examples the ether is diethylether and the solvents were removed in vacuo.

EXAMPLE 1

[[(2-(NonYloxy)phenyl]methyl]triohenvlphosphonium bromide

2-Hydroxybenzaldehyde (110 g), was alkylated by mixing this compound with 1-bromononane (180 g), anhydrous potassium carbonate and dimethylformamide (800 mL). This mixture was heated at 80oC for 14 hours. Hexane and water were then added and the hexane extract was concentrated and the residue was distilled to yield the 2-nonyloxybenzaldehyde (210 g), bp 121° C (0.3mm Hg). A solution of 2-nonyloxybenzaldehyde prepared above (100 g) in ethanol (1000 mL) at 10 C was reduced by treating with an excess of sodium borohydride (6 g) and after stirring the mixture for a further 15-20 min. at room temperature, the compound 2-nonyloxybenzylalcohol was isolated by extraction into hexane. Removal of the hexane in vacuo yielded the crude 2-nonyloxybenzylalcohol (98 g). The resulting 2-nonyloxybenzylalcohol was added to a mixture of triphenylphosphine hydrobromide (144 g) in acetonitrile (500 mL) and the resultant solution was heated at reflux for 14 hours. Removal of the solvents in vacuo and crystallization of the residue from a tetrahydrofuran/ethyl ether mixture gave the pure [[2-(nonyloxy)phenyl]methyl]triphenylphosphonium bromide (208 g).

EXAMPLE 2

[(2-Hydroxyphenyl)methyl]triphenylphosphonium bromide

2-Hydroxybenzyl alcohol was treated with triphenylphosphine hydrobromide in acetonitrile as described in Example 1 to yield [(2-Hydroxyphenyl)methyl]triphenylphosphonium bromide.

EXAMPLE 3

ALL(E)-9-(2-Hydroxyphenyl)-3,7-dimethyl-2,4,6,8-nonatetraenoic acid ethyl ester

A solution of [(2-hydroxyphenyl)methyl]triphenylphosphonium bromide (1 mol) in tetrahydrofuran was converted to the ylide at -35° with a solution of n-butyllithium in hexane (2.1 mol equiv.) and then exposed to 7-formyl-3-methyl-2,4,6-octatrienoic acid ethyl ester (1 mol) and then stirred at -70o for a further 15 min. Isolation of the organic products with a hexane/ethyl acetate mixture (4:1 parts by volume) and dilute mineral acid (2M aqueous HCl) gave the pure all(E)-9-(2-hydroxyphenyl)-3,7-dimethyl2,4,6,8-nonatetraenoic acid ethyl ester (90% yield) after chromatography followed by crystallization from a dichloromethane/hexane mixture.

EXAMPLE 4

ALL(E)-9-(2-Hydroxyphenyl)-3,7-dimethYl-2,4,6,8-nona tetraenoic acid ethyl ester A mixture of 2-hydroxybenzaldehyde (0.5 mol), (7-carboxy-2,6-dimethyl-2,4,6-heptatrien-1-yl)triphenylphosphonium bromide (0.6 mol) in 1,2-epoxybutane (750 mL) was heated at reflux for 30 min. cooled, poured into an ether/hexane mixture (1:1 parts by volume) filtered and concentrated. The residue was then crystallized from a hexane/ether mixture to yield all(E)-9-(2-hydroxyphenyl)-3, 7-dimethyl-2,4,6,8-nonatetraenoic acid ethyl ester (38% yield). mp 143–145°.

EXAMPLE 5

(All-E)-9-[2-(Nonyloxy)phenvl]-3.7-dimethyl-2.4.6.8-nonatetraenoic acid

A solution of [[2-(nonyloxy)phenyl]methyl]triphenylphosphonium bromide (150 g) in tetrahydrofuran (1100 mL) was cooled to −50° C to yield a fine suspension of the solid salt. To this mixture was added a solution of n-butyllithium in hexane (180 mL, a 1.6 molar) to yield a solution of the ylide. The mixture was then stirred a further 15 min at −40° C, cooled to −70° and treated with 7-formyl-3-methyl-2,4,6-octatrienoic acid ethyl ester (65 g) dissolved in tetrahydrofuran (250 mL). Addition of hexane and agueous methanol (40%) to the reaction mixture followed by concentration of the hexane extract yielded All(E)-9-[2-(nonyloxy)phenyl]-3,7-dimethyl-2,4,6,8-nonatetraenoic acid ethyl ester (64 g, 58% yield), mp 52–53° C. This ester was then hydrolized by forming a solution of this ester (70 g) in ethanol (1000 mL). This solution was treated with agueous potassium hydroxide (80 g in 400 mL water) and heated at reflux for 1 h. Water and aqueous mineral acid was then added and the solids were extracted into chloroform. Concentration of this organic extract and crystalization of the residue from an ethyl acetate hexane mixture yielded All(E)-9-[2-(nonyloxy)phenyl]-3,7-dimethyl-2,4,6,8-nonatetraenoic acid (38 g), mp 102–103° C.

EXAMPLE 6

(All-E)-9-[2-(Nonyloxy]phenyl]-3,7-dimethyl-2,4,6,8-nonatetraenoic acid

A mixture of sodium hydride (24 g, 50% by weight in mineral oil) and dimethylformamide (1000 mL) at 10° C was treated with All(E)-9-(2-hydroxyphenyl)-3,7-dimethyl-2,4, 6,8-nonatetraenoic acid ethyl ester (0.4 equiv.). The resulting mixture was then stirred at room temperature until all hydrogen evolution had stopped to produce the sodium salt of All(E)-9-(2-hydroxyphenyl)-3,7-dimethyl-2,4,6,8-nonatetraenoic acid ethyl ester. A solution of 1-nonyl tosylate (0.5 equiv.) in dimethylformamide (200 mL) was then added to this salt solution and the reaction mixture was stirred at 45o for 14 h. Hexane/water was then carefully added and the hexane extract was concentrated and the residue was purified by chromatography over silica gel. Crystallization from hexane then yielded the pure All(E)-9-[2-(nonyloxy)-phenyl]-3,7-dimethyl-2,4,6,8-nonatetraenoic acid ethyl ester. Hydrolysis of this ester as in Example 5 gave (All-E)-9-[2-(nonyloxy)phenyl]-3,7-dimethyl2,4,6,8-nonatetraenoic acid.

EXAMPLE 7

(All-E)-3,7-Dimethyl-9-[2-(2,2-dimethyl-octyl)oxY]ohenyl]2,4,5,8-nonatetraenoic acid 2-Hydroxybenzaldehyde was condensed with 2,2-dimethyl-1-iodo octane to yield 2-(2,2-dimethyl octyloxy) benzaldehyde which was reduced to 2-(2,2-dimethyl, octyloxy)benzyl alcohol and then converted to [[2-(2,2-dimethyloctyloxy)phenyl]methyl]triphenylphosphonium bromide as in Example 1. Condensation of this phosphonium bromide with 7-formyl-3-methyl-2,4,6-octatrienoic acid ethyl ester as described in Example 3 followed by hydrolysis, as in Example 5, gave the (All-E)-3,7-Dimethyl-9-[2-[(2,2dimethyl-octyl]phenyl]-2,4,5,8-non-atetraenoic acid mp 113-117° (from dichloromethane/hexane mixture).

EXAMPLE 8

(All-E)-3.7-Dimethyl-9-[2-[(octyloxy)-methvllphenyl]-2,4,6,8-nonatetraenoic acid Lithium octanoate. prepared from octanol and n-butyllithium, in a mixture of tetrahydrofuran/hexane dimethyl formamide was condensed with 2-bromobenzyl bromide to yield 2(octyloxy)methylbromobenzene. This material was treated with n-butyllithium in ether/hexane mixture and subsequently treated with paraformaldehyde to yield 2-(octyloxy)methylbenzyl alcohol. This material was then treated with triphenyl phosphonine bromide to yield [2-[(octyloxy)-methyl]-phenyl]methyl]triphenyl phosphonium bromide. Condensation of this material with 7-formyl-3-methyl-2,4,6-octatrienoic acid ethyl ester, as in Example 3, followed by hydrolysis, as in Example 5, gave the (All-E)-3,7-Dimethyl-9-[2-[(octyloxy)-methyl]phenyl]-2,4,6,8-nonatetraenoic acid, mp 120-121 (from dichloro methane/hexane mixture).

EXAMPLE 9

(All-E)-9-[2-chloro-6-(nonyloxy)phenyl]-3,7-dimethyl-2,4,6, 8-nonatetraenoic acid 2-chloro-6-hydroxy-benzaldehyde was alkylated with 1-bromononane as in Example 1 to give 2-chloro-6-nonyloxy benzaldehyde. Reduction with sodium borohydroxide as in Example 1 gave 2-chloro-6-nonyloxy benzyl alcohol which on treatment with triphenylphosphine hydrobromide in acetonitrile as in Example 1 yielded [[2-chloro-6-nonyl-oxy]phenyl]methyl]triphenyl phosphonium bromide. Condensation with 7-formyl-3-methyl-2,4,6-octatrienoic acid ethyl ester as described in Example 3 produced (All E)-9-[2-chloro-6-(nonyloxy)phenyl]-3,7-dimethyl-2,4,6,8-nonatetraenoic acid ethyl ester. The ester was subjected to hydrolysis, as in Example 5, to produce (All-E)-9-[2-chloro-6-(nonyloxy)phenyl]-3,7-dimethyl-2,4,6,8-nonatetraenoic acid mp 129-131° (from ethyl acetate/hexane mixture).

EXAMPLE 10

(All-E)-9-(5-Methoxv-2-nonyloxyphenyl)-3,7-dimethyl-2,4,6, 8-nonatetraenoic acid 5-Methoxy-2-hydroxybenzaldehyde was alkylated with nonylbromide and reduced with sodium borohydride, as in Example 1, to yield 5-methoxy-2-nonyloxy-benzyl alcohol which on exposure to triphenylphosphine hydrobromide gave [(5-methoxy-2-nonyloxyphenyl)methyl]triphenyl phosphonium bromide. Condensation of this material with 7-formyl-3-methyl-2,4,6-octatrienoic acid ethyl ester, as in Example 3, followed by hydrolysis, as in Example 5, gave (All-E)-9(5-Methoxy-2-nonyloxyphenyl)-3,7-dimethyl-2,4,6,8-nonatetraenoic acid mp 125-126o (from methanol).

EXAMPLE 11

All(E)-9-[2-(8-Hydroxyoctyl)oxY]phenyl-3.7-dimethyl-2.4.6. 8-nonatetraenoic acid The sodium salt of All(E)-9-(2-hydroxyphenyl)-3,7-dimethyl-2,4,6,8-nonatetraenoic acid ethyl ester in dimethylformamide prepared as described in Example 6 was treated with 1,8-dihydroxyoctane monotosylate as described previously in Example 6 and gave All(E)-9-[2-[8-hydroxyoctyl)oxy]phenyl-3,7-diethyl-2,4,6,8-nonatetraenoic acid ethyl ester after chromatography over silica gel. Hydrolysis as in Example 5 yielded All-(E)-9-[2-[(8-hydroxy-octyl)oxy]phenyl]-3,7-dimethyl-phenyl]- 3,7-dimethyl-2,4,6,8-nonatetraenoic acid, mp 122-123° (from ethyl acetate).

EXAMPLE 12

All(E)-[5-(2-NonvloxyphenVl)-3-methyl-2.4-pentadienyl]triphenyIphosphonium bromide 2-(nonyloxy)benzaldehyde (62 g) dissolved in acetone (500 mL) was treated with aqueous sodium hydroxide (100 mL, lM) at room temperature for 18 h. Brine an ethyl acetate/hexane (1:1 parts by volume) was then added. Concentration of the organic phase followed by crystallization from hexane gave 4-(2-nonyloxyphenyl)-3-butene-2-one (53 g).

A solution of 4-(2-nonyloxyphenyl)-3-butene-2-one (58 g) in tetrahydrofuran (200 mL) was added to a solution of vinylmagnesium bromide in tetrahydrofuran (200 mL, 1.6M diluted to lL with more tetrahydrofuran) at −30° C. After complete addition, the mixture was stirred at 0° C for 30 min qquenched with saturated aqueous ammonium chloride (100 mL) and ether (2L) and filtered free of solids. Concentration of the organic extract and purification by chromatography over siica gel yielded (E)-5-(2-nonyloxyphenyl)-3-hydroxy-3-methyl-1,4-pentadiene (40 g) as an oil.

A solution of (E)-5-(2-nonyloxyphenyl)-3-hydroxy-3methyl-1,4-pentadiene (66 g) in acetonitrile (250 mL) was added to a slurry of triphenylphosphine hydrobromide (66 g) in more acetonitrile (300 mL) at 10° C. After warming to room temperature, the mixture was stirred at this temperature for 2h to yield a solution. This solution was then extracted with hexane (2×250 mL) and the acetonitrile layer was concentrated (ca. 400 mL) and cooled to −10°. The solids were filtered off, washed with acetonitrile, hexane, and dried to give pure All(E)-[5-(2-nonyloxyphenyl)3-methyl-2,4-pentadienyl]triphenylphosphonium bromide (21 g).

EXAMPLE 13

Starting with All(E)-[5-(2-nonyloxyphenyl)-3-methyl 2,4-pentadienyl]triphenylphosphonium bromide and utilizing the procedure of Example 5, the ylide was reacted with 3-formyl-2-butenoic acid ethyl ester to yield All(E)-9-(2-nonloxyphenyl)-3,7-dimethyl-2,4,6,8-nonatetraenoic acid after purification by chromatography over silica gel and hydrolysis with aqueous ethanolic potassium hydroxide solution as in Example 5.

EXAMPLE 14

(Z,E,E,E)-9-2-(Nonyloxy)phenyl]-3,7-dimethyl-2,4,6,8-nonatetraenoic acid

All(E)-9-[2-(nonyloxy)phenyl]-3,7-dimethyl 2,4,6,8nonatetraenoic acid ethyl ester (10 g) was dissolved in hexane (200 mL) containing iodine (0.5 g) and stirred at room temperature for 30 min. The hexane was washed free of iodine with an aqueous sodium thiosulfate solution (10% by weight), dried and concentrated to give a mixture of double bond isomers. Separation, by chromatography on silica gel, yielded pure (Z,E,E,E)-9-[2-(nonyloxy)phenyl]-3,7-dimethyl-2,4,6,8-nonatetraenoic acid ethyl ester (1.5 g). Hydrolysis with aqueous ethanolic potassium hydroxide at reflux gave the pure (Z,E,E,E)-9-[2-(nonyloxy)phenyl]-3,7-dimethyl-2,4,6,8-nonatetraenoic acid: mp 135–136° C.

EXAMPLE 15

(E,E,E,Z)-9-[2-(Nonyloxy)phenyl]-3,7-dimethyl-2,4,6,8-nonatetraenoic acid

The mother liquor material resulting from the crystallization of All(E)-9-[2-(nonyloxy)phenyl]-3,7-dimethyl-2,4,6,8-nonatetraenoic acid ethyl ester in Example 5 was a mixture containing various isomers. Purification by chromatography yielded an 80% pure ethyl ester which after hydrolysis as in Example 5 yielded pure (E,E,E,E,Z)-9[2(nonyloxy)phenyl]-3,7-dimethyl-2,4,6,8-nonatetraenoic acid: mp 105–109°.

EXAMPLE 16

2-Decyl-1-bromobenzene

Nonylmethyltriphenyl phosphonium bromide (0 1 mol) in tetrahydrofuran (200 mL) was converted to the ylide with n-Butyllithium (0.1 mol equiv; 1.6M in hexane) at −10° C.

2-Bromobenzaldehyde (0.09 mol) was then added in tetrahydrofuran (25 mL) and after the mixture had been stirred for a further 30 min at 0 C hexane and aqueous methanol (40:60) was added. The hexane extract was concentrated and the residue was distilled to yield 2-(1-decenyl)-1-bromobenzene (90%).

This material was dissolved in hexane containing a palladium on carbon catalyst (10%) and hydrogenated at room temperature and pressure until the olefinic link was saturated. The solids were filtered off and removal of the hexane and distillation of the residue gave pure 2-decyl-1-bromobenzene (80%): bp 120° (0.001 mm Hg).

EXAMPLE 17

2-Decyl-1 hYdroxymethylbenzene

2-Decyl-1-bromobenzene (0.1 mol) dissolved in ether (150 mL) was treated with n-butyllithium (0.11 eq. 1.6M in hexane) and the mixture was stirred at room temperature for 2 hours.

Dry paraformaldehyde (0.2 mol eq) was then added and the mixture was srirred for a further 18h at room temperature.

Water and move ether was then added and the ether extracts were dried and concentrated. The residue after chromatography yielded pure 2-decyl-1-hydroxy methyl benzene (75% yield).

EXAMPLE 18

All(E)-9-(Decyphenyl)-3.7-dimethyl-2.4.6.8-nonatetraenoic acid

2-Decyl-1-hydroxymethylbenzene was converted to the phosphonium salt with triphenylphosphonium hydrobromide in acetonitrile by the procedure of Example 1. This salt was then exposed to n-butyllithium in tetrahydrofuran as before and then treated with 7-formyl-3-methyl-2,4,6-heptatrienoic acid methyl ester as before.

Purification of the crude condensation product by chromatography on silica gel followed by basic hydrolysis yielded pure All(E)-9-(decylphenyl)-3,7-dimethyl-2,4,6,8-nonatetraenoic acid: mp 107–108° (from hexane-ether).

EXAMPLE 19

All(E)-9-(2-octylaminophenyl)-3,7-dimethyl-2,4,6,8-nonatetraenoic acid ethyl ester 2-Aminobenzyl alcohol (1 mol) was treated with octanoylchloride (2.2 mol) in a mixture of dichloromethane-triethylamine at 0° C After 30 min at 10° C the mixture was washed with water and the ether was distilled off. The crude residue was dissolved in tetrahydrofuran (2000 ml). treated with aqueous sodium hydroxide (lN, 1500 mL) and stirred at room temperature for 3h.

Addition of water and ether yielded the crude hydroxymethyl octylamide. Purification by chromatography yielded the pure octyamide (85%).

This material (100 g) was dissolved in tetrahydrofuran (500 mL) and added to a slurry of Lithium aluminum hydride (2 mol equiv) in tetrahydrofuran (1000 mL). The mixture was then heated at reflux for 8h cooled to 0° C and quenched with aqueous sodium sulfate solution (100 mL).

The solids were filtered off, the solvents were removed in vacuo and the residue was purified by chromatography on silica gel to yield pure 2-hydroxymethyl-N-octylamaline (75g).

This material was dissolved in acetonitrile (300 mL) containing triphenyl phosphine hydrobromide (1.1 eq) and the mixture was heated at reflux for 24h and then concentrated. The residue was digested with ether to give the phosphonium salt as a white solid.

This material was converted to the corresponding ylide with n-butyllithium (1.5 mol eq) and stirred at 0° for 1h. Excess 7-formyl-3-methyl-2,4,6-heptatrienoic acid ethyl ester (1.6 mol eq) was then added in tetrahydrofuran and the mixture was stirred at 10° C for 1h.

Addition of hexane and aqueous methanol (2:3) and removal of the hexane in vacuo gave the crude coupled product. Purification by chromatography on silica gel and crystallization from hexane gave pure ALL(E)-9-(2-octyl amino phenyl)-3,7-dimethyl-2,4,6,8-nonatetraenoic acid ethyl ester (25%): mp 38–40° C.

EXAMPLE 20

2-Fluoro-6-nonyloxybenzyl alcohol

A solution of 3-fluoro phenol (100 g) in dimethylformamide (1000 mL) containing potassium carbonate (165 g) was treated with allyl bromide (115 g) and heated at 80° for 18 hours.

Water and hexane were then added and the hexane extract was washed with aqueous sodium hydroxide solution (5%), saturated brine solution and concentrated to yield the allyl ether (155 g). This material (134 g) was heated at 220° for 16 hours to yield a mixture of 3-fluoro-2-(2-butenyl)phenol and 5-fluoro-2-(2-butenyl)phenol. This mixture was dissolved in dimethyl formamide (2000 mL) containing 1-bromononane (170 g) and potassium carbomate (150 g) and heated at 80o for 16 hours. Dilution with water and extraction with hexane yielded a mixture of products on concentration. Distillation gave a mixture of 3-[(2-fluoro-6-nonyloxy)-phenyl]-butene and 3-[(3-fluoro]-2-nonyloxy)phenyl]-butene (186 g) bp. 120°–125° @ 0.1mm.

This mixture of isomers (185 g) in dimethylsulfoxide (1000 mL) containing potassium tert-butoxide (1.5 g) was left at room temperature for 6 hours. Addition of water and extraction with hexane gave the mixture of 1-[(2-fluoro-6-nonyloxy)phenyl]-butene and 1-[(3-fluoro-2-nonyloxy)phenyl]butene.

This mixture of isomers (175 g) was dissolved in a mixture of dichloromethane and methanol (9:1, 2000 mL) and exposed to a stream of ozone at −40° for 8h. After this time the reaction mixture was poured into a mixture of water, hexane and dimethylsulfide (100 mL) and stirred at room temperature for 1 hour.

The hexane extract was washed (water), dried (MgSO$_4$), treated with more dimethyl sulfide (50 mL) and left at room temperature for 16 hours.

Removal of the solvents yielded the mixture of aldehydes 2-fluoro-6-nonyloxybenzaldehyde and 4-fluoro-2-nonloxy-benzaldehyde (155 g).

This mixture of aldehydes (150 g) in ethanol (2000 mL) was exposed to sodium borohydride (15 g) at 5° and then stirred at room temperature for 30 min. Water (1500 mL), brine (500 mL) were then added and the mixture of alcohols was extracted into hexane. Removal of the solvents and chromatography of the residue over silica gel (5% ethylacetate-hexane mixture) yielded pure 2-fluoro-6-nonyloxy-benzyl alcohol (76 g).

EXAMPLE 21

(All-E)-9-2-Fluoro-6-(nonyloxy)phenyl]-3,7-dimethyl-2,4,6, 8-nonatetraenoic acid A mixture of 2-fluoro-6-nonyloxybenzyl alcohol (19 g) and triphenylphosphine hydrobromide (26 g) in acetonitrile (250 mL) was heated at reflux for 14 hours and then concentrated to dryness to yield [[(2-fluoro-6-nonyloxy)phenyl]methyl]triphenyl phosphonium bromide (42 g). This phosphonium salt was.dissolved in tetrahydrofuran (600 mL) cooled to −50o and treated with n-butyllithium (45 mL, 1.6M in hexane). After stirring a further 15 min at −50° 7-formyl-3-methyl-2,4,6-octatrienoic acid ethyl ester (8.4 g) was added and the reaction mixture was warmed to room temperature and stirred for a further 15 min. Hexane was then added and the mixture was washed with water, 40% aqueous methanol and dried (MgSO$_4$). Concentration of the hexane extract and purification by chromatography (5% ether-hexane) gave the pure trans isomer (11 g).

Crystallization from hexane-ethyl acetate gave (All-E)-9-[2-fluoro-6-(nonyloxy)-phenyl]-3.7-dimethyl-2,4,6,8-nonatetraenoic acid ethyl ester (9.5 g).

A solution of the ester (6.5 g) in ethanol (150 mL) was treated with a solution of potassium hydroxide (7 g) in water (40 mL) and heated at reflux for 1 hour. The cooled reaction mixture was poured into cold aqueous hydrochloric acid and the acid was extracted into chloroform. Removal of the solvents and crystallization from hexane-ethyl acetate gave pure (all-E)-9-[2-fluoro-6-(nonyloxy)phenyl]-3,7-dimethyl-2,4,6,8-nonatetraenoic acid mp 107–109°.

EXAMPLE 22

| CAPSULE FORMULATIONS: | | | | |
|---|---|---|---|---|
| Item | Ingredients | mg/capsule | mg/capsule | mg/capsule |
| 1. | (All E)-9-[2-(nonyloxy)phenyl]-3,7-dimethyl-2,4,6,8-nonatetraenoic acid | 15 | 30 | 60 |
| 2. | Lactose | 239 | 224 | 194 |
| 3. | Starch | 30 | 30 | 30 |
| 4. | Talc | 15 | 15 | 15 |
| 5. | Magnesium | 1 | 1 | 1 |
| | Capsule fill weight | 300 mg | 300 mg | 300 mg |

PROCEDURE:
(1) Mix items 1–3 in a suitable mixer.
(2) Add talc and magnesium stearate and mix for a short period of time.
(3) Encapsulate on an appropriate encapsulation machine.

EXAMPLE 23

Capsules are prepared by the procedure of Example 22 except that the active ingredient (item 1) was (All E)-9-[2-fluoro-6[nonyloxy)phenyl]-3,7-dimethyl-3,4,6,8-nonatetraenoic acid.

EXAMPLE 24

| TABLET FORMULATION (Wet granulation) | | | | |
|---|---|---|---|---|
| Item | Ingredients | mg/tablet | mg/tablet | mg/tablet |
| 1. | (All E)-9-[2-(nonyloxy)phenyl]-3,7-dimethyl-2,4,6,8-nonatetraenoic acid | 100 | 250 | 500 |
| 2. | Lactose | 98.5 | 147.5 | 170 |
| 3. | Polyvinyl pyrrolidone (PVP) | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Weight of tablet | 245 mg | 490 mg | 795 mg |

Procedure:
1. Mix items 1, 2, 4 and 5 in a suitable mixer, granulate with PVP and dissolve in water/alcohol. Dry the granulation. Mill the dry granulation through a suitable mill.
2. Add magnesium stearate and compress on a suitable press.

EXAMPLE 25

Tablet are prepared in the same manner as Example 24 except that the active ingredient (item 1) was (All E)-9-[2-fluoro-6(nonyloxy)phenyl]-3,7-dimethyl-2,4,6,8-nonatetraenoic acid.

EXAMPLE 26

| TABLET FORMULATIONS: (Direct Compression) | | | | |
|---|---|---|---|---|
| Item | Ingredient | mg/tablet | mg/tablet | mg/tablet |
| 1. | (All E)-9-[2-(nonyloyl)phenyl]-3,7-dimethyl-2,4,6,8-nonatetraenoic acid | 15 | 30 | 60 |
| 2. | Lactose | 207 | 192 | 162 |
| 3. | Avicel | 45 | 45 | 45 |
| 4. | Direct Compression Starch | 30 | 30 | 30 |
| 5. | Magnesium | 3 | 3 | 3 |
| | Weight of tablet | 300 mg | 300 mg | 300 mg |

PROCEDURE:
1. Mix Item 1 with equal amount of lactose. Mix well.
2. Mix with Item 3, 4, and remaining amount of Item 2. Mix well.
3. Add magnesium stearate and mix for 3 minutes.
4. Compress on a suitable punch.

EXAMPLE 27

CAPSULE FORMULATIONS:

| Item | Ingredients | mg/capsule | mg/capsule | mg/capsule |
|---|---|---|---|---|
| 1. | (All E)-(3,7-dimethyl)-9-[2[(8-hydroxy-octyl)oxy]Phenyl]-2,4,6,8-nonatetraenoic]acid. | 15 | 30 | 60 |
| 2. | Lactose | 239 | 224 | 194 |
| 3. | Starch | 30 | 30 | 30 |
| 4. | Talc | 15 | 15 | 15 |
| 5. | Magnesium | 1 | 1 | 1 |
| | Capsule fill weight | 300 mg | 300 mg | 300 mg |

PROCEDURE:
(1) Mix items 1-3 in a suitable mixer.
(2) Add talc and magnesium stearate and mix for a short period of time.
(3) Encapsulate on an appropriate encapsulation machine.

EXAMPLE 28

TABLET FORMULATIONS (Wet granulation)

| Item | Ingredient | mg/tablet | mg/tablet | mg/tablet |
|---|---|---|---|---|
| 1. | (All E)-3,7-dimethyl-9-[2,[(octyloxy)methyl]Phenyl]-2,4,6,8-nonatetraenoic acid | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Weight of tablet | 245 mg | 490 mg | 795 mg |

Procedure:
1. Mix items 1, 2, 4 and 5 in a suitable mixer, granulate with PVP and dissolve in water/alcohol. Dry the granulation. Mill the dry granulation through a suitable mill.
2. Add magnesium stearate and compress on a suitable press.

EXAMPLE 29

[[2-Trifluoromethyl-6-(nonyloxy)phenyl]methyl]triphenylphosphonium bromide

A mixture of α, α, α-trifluoro-m-cresol (51 g), 1-bromononane (70 g), potassium carbonate (100 g) in dimethylformamide was heated at 85° C for 48 h. Addition of water and hexane gave pure (3-trifluoromethyl) phenyl nonyl ether (89 g): b.p. 115° C at 0.1 mmHg. This product (89 g) in ether (1.5 L) at −20° C was mixed with n-butyllithium (1.5 M in hexane; 233 mL) and then stirred for 2h at room temperature. This mixture was then cooled to −40°, treated with an excess of dry dimethylformamide (40 mL) in ether (100 mL), warmed to 0° and then treated with water. Extraction with hexane and chromatography on silica (5% ether-hexane) gave (2-trifluoromethyl-6-nonyloxy)benzaldehyde (35 g). Reduction of this product with sodium-borohydride is ethanol by the procedure set forth in Example 1 gave (2-trifluoromethyl-6-nonyloxy)benzenemethanol (32 g) after chromatography over silica. This material (31 g) was converted into [[2-trifluoromethyl-6(nonyloxy)phenyl]methyl]triphenylphosphonium bromide by reaction with triphenylphosphine hydrobromide by the procedure given in Example 1.

EXAMPLE 30

(All-E)-9-[2-(Trifluoromethyl)-6-(nonyloxy)phenyl]-3,7-dimethyl-2,4,6,8-nonatetraenoic acid

[[2-trifluoromethyl-6-(nonyloxy)phenyl]methyl]triphenylphosphonium bromide (97 mmol) in tetrahydrofuran (600 mL) was converted by reaction with 7-formyl-3-methyl-2,4,6-octatrienoic acid ethyl ester to (All-E)-9-[2-(trifluoromethyl)-6-(nonyloxy)phenyl]-3,7-dimethyl-2,4,6,8-nonatetraenoic acid ethyl ester by the procedure given in Example 3. Purification by chromatography and crystallization from hexane gave the pure ethyl ester (41%). Hydrolysis (5.2 g) as in example 5 gave pure (All-E)-9-[2-(trifluoromethyl)-6-(nonyloxy)phenyl]-3,7dimethyl-2,4,6,8-nonatetraenoic acid (3 g): mp 135-136 (from ethyl acetate hexane).

EXAMPLE 31

(All-E)-9-[2-(hexyloxy)ohenyl]-3,7-dimethyl-2,4,6,8-nonatetraenoic acid

[[2-(hexyloxy)phenyl]methyl]triphenylphosphonium bromide, prepared by the procedure of Example 1 by reacting 2-hydroxybenzaldehyde and 1-bromohexane, was converted to (All-E)-9-[2-(hexyloxy)phenyl]-3,7-diethyl-2,4,6,8-nonatetraenoic acid, mp 137-138° (from ethanol) by the procedure of Example 3.

EXAMPLE 32

[[2-(Nonyloxy)-5-(hydroxy)ohenyl]methyl]triphenylphosphonium bromide

A solution of 4-bromophenol (1 mol) in tetrahydrofuran (500 mL) was added to a slurry of sodium hydride (1.17 mol) in dimethylformamide (1.2 L) at 25° C. After complete reaction allylchloride (1.32 mol) was added and after stirring for a further 3 h at 45° the product was isolated with water and hexane. Distillation gave allyl-(4-bromophenyl)ether. bp. 65-67° at 0.1 mm (82%). This material was heated at 195° with dimethylanaline for 4 hours and then distilled to yield 2-allyl-4-bromophenol (0.81 mol). A solution of this material (0.81 mol) in tetrahydrofuran (200 mL) was added to a mixture of 1-bromononane (0.8 mol), sodium hydride (0.92 mol) potassium iodide (1 g) in dimethylformamide (1L) at 25° C After hydrogen evaluation was complete the mixture was heated at 50o for 14 h, cooled, added to an excess of water and extracted with hexane. Distillation furnished nonyl-(2-allyl-4-bromophenyl)ether (256 g): b.p. 147-156° at 0.1 mm. This material (255 g) in dimethylsulfoxide (1 L) and tetrahydrofuran (0 5 L) was heated at 35-40° with potassium tert. butoxide (2 g) for 2 h and then quenched with acetic acid (5 mL) and water. Isolation of the reaction products with hexane yielded pure 1-[2-(nonyloxy)-5-(bromo)phenyl]propene (234 g): b.p. 145-155° at 0.1 mm. A solution of the above material (0.56 mol) in tetrahydrofuran (600 mL) was converted to the Grignard reagent with magnesium (1 mol) at 55 C for 3 h. After complete reaction the mixture was cooled to 0° C and treated with trimethylborate (0.75 mol) in ether (200 mL). After stirring for a further 30 min. at 25° C the mixture was cooled to 0° and exposed to a mixture of ammonium chloride (10%) and hydrogen peroxide (10%, 500 mL) and stirred for a further 1h at 25oC Addition of water and hexane gave the crude material after removal of the hexane in vacuo. The crude product was passed through a plug of silica gel to yield para [2-(1-propenyl-4-(nonyloxy)phenyl]phenol (73 g). Acetylation of this material (0.8 g) with acetylchloride and triethylamine in dichloromethane gave the [2-(1-propenyl)-4-(nonyloxy)-1-(acetoxy)]benzene (89%). This material (99 g) was dissolved in a mixture of methanol (150 mL) and dichloromethane (1.5 L) and treated with ozone at −40° C until all the starting material had been consumed. Dimethylsulfide (50 mL) and water (500 mL) were then added and after vigorous stirring for 30 min. at 25° the organic phase was dried (MgSO4) and concentrated to yield [2-(nonyloxy)-5-(acetoxy)]-benzaldehyde (83 g). Reduction of this material (80 g) with sodium borohydride (6 g) in ethanol (1L) at 20° C for 2 h gave the crude [2-(nonyloxy)-5-(acetoxy)]benzenemethanol which was immediately exposed to aqueous potassium hydroxide (300 mL, 40%) in ethanol (1L) for 30 min at 60° C. Acidification with aqueous acid (6 Molar hydrogen chloride) and extraction with chloroform yielded the crude product on concentration. Digestion of the residue with hexane gave pure [3-(hydroxymethyl)-4-(nonyloxy)]phenol (63 g) as a solid. A solution of this material (62 g) in a mixture of acetonitrile (0.5 L) and trihenylphosphine hydrobromide (86 g) was heated at reflux for 14 h and concentrated to dryness at 50° C to yield [[2-(nonyloxy)-5(hydroxy)-phenyl]methyl]triphenylphosphonium bromide as a glass.

EXAMPLE 33

(All-E)-9-[5-Hvdroxy-2-(nonyloxy)phenyl]-3,7-dimethyl-2,4,6,8nonatetraenoic acid The [[2-(nonyloxy)-5-(hydroxy)phenyl]methyl]triphenylphosphonium bromide (0.23 mol) in tetrahydrofuran (1.5 L) at −70 C was treated with n-butyllithium (1.6M in hexane; 315 mL) and then treated with ethyl 8-formyl-3,7-dimethyl-2,4,6-octatrienoate (59 g) in tetrahydrofuran. The mixture was then warmed to -15oC acidified with acetic acid and extracted into ether and aqueous methanol (40%). Purification by chromatography over silica gel gave pure (All-E)-9-[5-hydroxy-2(nonyloxy)phenyl]-3,7-dimethyl2,4,6,8-nonatetraenoic acid ethyl ester. Hydrolysis of this ester (6 g) by the procedure given in Example 5 gave (All-E)-9-[5-hydroxy-2(nonyloxy)phenyl]-3,7-dimethyl-2,4,6,8-nonatetraenoic acid (3.5 g): mp 170–173° (from ethylacetate).

EXAMPLE 34

(All-E)-9-[2-(nonyloxy)-5-(2,2,2-trifluoroethoxy)-phenyl]-3,7-dimethyl-2,4,6,8-nonatetraenoic acid (All-E)-9-[5-hydroxy-2-(nonyloxy)phenyl]-3,7-dimethyl-2,4, 6,8-nonatetraenoic acid ethyl ester (4.4 g) was heated at 90° C for 72 h with potassium carbonate (7 g), 2,2,2-trifluoroethyl-p-toluensulphonate (6 g) in dimethylformamide (200 mL). Work up with water and hexane followed by purification over silica gave the pure ethyl ester (0.75 g). Hydrolysis of this ester (0.9 g) by the procedure of Example 5 gave pure (All-E)-9-[2-(nonyloxy)5(2,2,2-trifluoroethoxy)phenyl]-3,7-dimethyl-2,4,6,8-nonatetra enoic acid (0.6 g) after crystallization from a mixture of tetrahydrofuran and hexane: mp 121° C.

EXAMPLE 35

(Z)-2-(1-Decenyl)phenyl]methyl]-triphenylphosphonium bromide and
(E)-[[2(1-Decenyl)phenyl]methyl]triphenylphosphonium bromide An (E,Z) mixture of 2-(1-decenyl)-1-bromobenzene as prepared in Example 16 ( 1:4) was converted to a (E,Z) mixture of 2-(1-decenyl)-1-hydroxymethyl benzene by the procedure of Example 17. This mixture was separated by chromatography on silica gel to yield the pure (E) and (Z) alcohols. Reaction of each of these isomers with triphenylphosphine hydrobromide as in example 1 gave the corresponding phosphonium salts i.e. (Z)[[2-(1-decenyl)phenyl]methyl]-triphenylphosphonium bromide and (E)[[2-(1-decenyl)phenyl]methyl]triphenylphosphonium bromide.

EXAMPLE 36

(All-E)-9-[2-(1-Decenyl)ohenyl]-3,7-dimthyl-2,4,6,8-nonatetraenoic acid

The (E)-[[2-(1-decenyl)phenyl]methyl]-triphenylphosphonium bromide was converted into the ethyl ester of (All E)-9-[2-(decenyl)phenyl]-3,7-dimethyl-2,4,6,8-nonatetraenoic acid by the procedure given in Example 1. Hydrolysis with base as in Example 1 and crystallization of the crude acid from acetonitrile gave (All-E)-9-[2-(1-decenyl)phenyl]-3,7-dimethyl-2,4,6,8-nonatetraenoic acid, mp 105-107.

EXAMPLE 37

(E,E,E,E,Z)-9-[2-(1-Decenyl)phenyl]-3,7-dimethyl-2,4,6,8nonatetraenoic acid

The title compound was prepared in the same manner as in Example 36 employing the (Z)-[[2-(1-decenyl)-phenyl]methyl]triphenyl phosphonium bromide. Hydrolysis of the ethyl ester and crystallization of the crude acid from ether yielded pure (E,E,E,E,Z)-9-[2-(1-decenyl)phenyl]-3,7-dimethyl-2,4,6,8-nonatetraenoic acid, mp 103–105°.

In the following examples, Compound A is All(E)-9(nonyloxy)phenyl]-3,7-dimethyl-2,4,6,8-nonatetraenoic acid. In the following examples, Compound A was tested by various tests for its anti-inflammatory activity in animal models of inflammation and in certain chronic models for adjuvant arthritis.

In all tests, Compound A and the other retinoids tested concurrently were formulated in arachis oil containing 0.05% propylgallate as anti-oxidant. The dose volumes used were 5 ml.kg$^{-1}$ for rats and 10 ml.kg$^{-1}$ for mice. Controls were dosed with the appropriate volume of arachis oil vehicle.

EXAMPLE 38

Effect of Compound A on delayed hypersensitivity to methylated bovine seru albumin (MBSA)

Animals — Male and female MFI mice substrain E33. Initial weight approximately 25 gm.
Materials — Methylated bovine serum albumin (MBSA) (Sigma) Freunds complete adjuvant (Difco)
Method — Groups of 10 mice were sensitized (day 0) by injecting intradermally at two abdominal. sites 0.05 ml. of a water in oil emulsion of MBSA and Freunds complete adjuvant. On day 9 the mice were challenged by injecting 20 1 of a 1% MBSA solution to one paw and 20 l of water into the contralateral paw. Paw volumes were measured 24 hours later by mercury displacement plethysmography. The means percentage increase in paw volume of the MBSA-challenged paw compared with the water challenged paw was calculated for each treatment group. Dosing with vehicle and retinold commenced on day 0 and finished on day 9.

Results — The results are given in the following table (Table II)

TABLE II

The effects of Compound A in the MBSA delayed hypersensitivity test

| Treatment | Dose mg.kg$^{-1}$ | % incerase paw volume | % (cf. arachis oil control) | Mean body weight (g) |
|---|---|---|---|---|
| Arachis Oil | | 109 ± 11 | | M 3.8 F 0.2 |
| Etretinate | 10 | 59 ± 9** | 46 | M −0.8 F −2.0 |
| Compound A | 10 | 102 ± 12$^{ns}$ | 6 | M 3.3 F −0.2 |
| Compound A | 30 | 50 ± 7*** | 54 | M 2.8 F 0.5 |
| Compound A | 100 | 40 ± 5*** | 63 | M 3.3 F −0.2 |

Each group consisted of 4 male and 6 female mice (separately caged). Drugs were dosed orally at a dose volume of 10 ml.kg$^{-1}$ (10 doses). ns. Not significant p<0.01 *p<0.001 compared with vehicle control using Student's two-tailed t test.

EXAMPLE 39

Effect of Compound A on developing adjuvant arthritis in the rate.

Animals—AHH/R Female rats (PVG derived with an initial weight range of 110 to 140 g. were used.

Materials—Adjuvant for injection. An homogenized suspension of heat killed M. tuberculosis (Human strains C, DT and PN), 5 mg.Ml$^{-1}$ in liquid Paraffin was Prepared.

Method Rats were randomly split into groups of five and adjuvant arthritis was induced by the sub-plantar injection of 0.1 ml of adjuvant susPension into the right hind paw of each rat. Test compounds were administered by intubation each morning commencing the day of adjuvant injection. Two groups of control rats were dosed with the vehicle as was a group of three normal rats included for comparative purposes. Dosing was carried out daily until the end of the test on day 15 except for the first weekend (days 5 & 6). Treatment groups are shown in Table III and include etretinate as standard retinoid.

Measurements of right hind paw volume were made initially and on days 2 and 4 after and adjufant injection (primary phase). Right and left hind paw volume were then measured on day 8 and every two or three days until the end of the experiment on day 15 (secondary phase). At this time the mobility of each ankle joint and the incidence and severity of secondary lesions on nose, ears, forepaws, left hind paw and tail were also assessed in terms of degrees of flexion possible and by using an arbitrary scoring system, respectively.

Assessment of results

The time course curves for the injected paws were integrated from days 0 to 4 to reflect primary swelling and from days 8 to 15 (secondary swelling). The secondary swelling in the non-injected paw was integrated similarly from days 8 to 15. Calculations were carried out using a specific computer program which computed mean ± se for each integrated area. The significance of differences from controls was determined by Student s t test (2 tailed) and percentage reductions from control areas were calculated. Percentage improvements in joint mobility and percentage reductions in lesion score were also determined. In the latter case the Wilcoxon rank sum test (2 tailed) was used to express the difference from the control score using raw data. Mean body weight change in each group was recorded.

Results — The results are given in the following table (Table III)

TABLE III

Effect of Compound A and ertretinate on adjuvant arthritis in the rat

| Treatment | Dose mg.kg$^{-1}$p.o. | % reduction of paw swelling[1] | | | Lesion[2] Score (% RDN) | Joint[1] Mobility (% INC) | Body Weight Change (g) | |
| | | Primary (right) | Secondary (left) | Secondary (right) | | | Days 0–15 | Days 8–15 |
|---|---|---|---|---|---|---|---|---|
| Normal Control | — | — | — | — | — | — | +13.3*** | +3.7*** |
| Adjuvant | — | — | — | — | — | — | −0.6 | −5.5 |
| Compound A | 15 | −6 | 30 | 94*** | 72* | 66** | +2.2 | −0.4 |
| | 45 | 16 | 51*** | 75** | 65* | 66** | +5.4 | +1.2* |
| Ertretinate | 15 | 9 | 30 | 67* | 56* | 50 | +1.0 | −5.0 |

[1]Statistical analysis by students 't' test (2-tailed)
[2]Statistical analysis by Wilcoxon rank sum test (2-tailed)
*= P < 0.05 = P < 0.02 *= P < 0.01

EXAMPLE 40

Effect of Compound A on established type II collagen arthritis

Animals — Male and female Alderley Park Strain 1 rats.

Materials — Type 2 collagen (prepared from bovine nasal septum cartilage), Freunds incomplete adjuvant (Difco).

Method — Rats were sensitized to type 2 collagen by injecting them intradermally with 1 ml. of a water in oil emulsion consisting of equal parts of a 1 mg.ml$^{-1}$ solution of type 2 collagen in 0.45M NaCl, 0.02M Tris, PH 7.4 and Freunds incomplete adjuvant. Rats developing arthritis were allocated on day 15 post sensitization to a control arachis oil treated group (6 male, 4 female) or to the Compound A treated group (6 male, 5 female). Hind paw volume measurements were taken to ensure even distribution of rats between groups. An overnight collection of urine was made on days 15/16 and dosing commenced on day 16. These urine samples were analyzed for glycosaminoglycans (GAG). Compound A was dosed at 100 mg.kg$^{-1}$ p.o. On days 19/20 a second overnight collection of urine was made. These urine samples were analyzed for glycosaminoglycans (GAG). On day 20 a second hind paw measurement was taken. Rats were then anaesthetised with sodium pentobarbitone, bled, killed and X-rays taken of hind and forepaws. Rats were dosed on days 16-19 inclusive (4 doses).

Results — The results are given in the following table (Table IV).

TABLE IV

The effects of Compound A in the type II collagen arthritis test

| DAY | Compound A 100 mg.kg$^{-1}$ | | | CONTROL Arachis Oil | | |
|---|---|---|---|---|---|---|
| | Paw Vol | GAG (μg) | wt (g) | Paw Vol | GAG (μg) | wt (g) |
| 16 | 2.44 ± 0.08 | 1586 ± 307 | 247 ± 14 | 2.48 ± 0.07 | 1538 ± 192 | 249 ± 19 |
| 20 | 2.66 ± 0.06 | 634 ± 72 | 229 ± 10 | 2.46 ± 0.07 | 729 ± 134 | 258 ± 19 |

Comment. Both male and female rats lost weight during treatment with Compound A.

EXAMPLE 41

Effect of Compound A on non-immune inflammation

Animals — Female Alderley Park Strain 1 rats weighing 170-205 g. at the start of the experiment were used.

Materials — Lambda -carrageenan. Prepared as a solution in saline and sterilized by autoclaving.

Method — Compound A was administered orally to groups of 8 rats once daily for 10 days at doses of 10, 30 and 100 mg.kg$^{-1}$. Control animals received the vehicle. One hour after the last dose the animals were anesthetised with methohexitone (Brietal, 50 mg.kg$^{-1}$) and 0.2 ml of 1% lambda carrageenan was injected into the pleural cavity. Four hours later the animals were killed with an overdose of pentobarbitone (Sagatal), the pleural exudate was collected and the pleural cavity was washed out with 2 ml of phosphate-buffered saline (PB$-A, Oxoid). The exudate volume was recorded and cell counts were determined using an automatic cell counter (Coulter). Differential cell counts were performed on exudate smears stained with Giemsa stain in order to determine separately the numbers of polymorphonuclear leucocytes (PMN) and mononuclear cells (MN).

Immediately after recovery of the pleural exudates the tibiae of the animals were excised and their breaking strains were determined.

The body weights of the animals were recorded daily. Statistical analyses were performed using Student's two-tailed t test.

Results — The results are given in the following table (Table V). In the following table the dose is in mg per kg per day.

TABLE V

The effects of Compound A on the development of 4 hr carrageenan pleurisy

| Compound | Dose (p.o.) | Exudate Volume (ml) | % change | Total Cell Count ×10$^6$ | % change | Total PMN ×10$^6$ | % change | Total MN ×10$^6$ | % change | Tibial Breaking Strain (Right + Left) Mean (kg) | % change |
|---|---|---|---|---|---|---|---|---|---|---|---|
| Control (Arachis oil) | 5 ml | 1.40 ± 0.16 | | 129.3 ± 3.1 | | 119.1 ± 2.9 | | 10.2 ± 0.3 | | 6.7 ± 0.3 | |
| Compound A (Solution) | 10 mg | 0.94* ± 0.08 | −32.8 | 120.8 ± 7.3 | N.S. −6.5 | 112.4 ± 6.7 | N.S. −5.6 | 8.4 ± 0.8 | N.S. −17.4 | 6.5 ± 0.1 | N.S. −3.4 |
| Compound A | 30 mg | 0.88* ± 0.09 | −36.9 | 112.1* ± 6.0 | −13.3 | 104.2* ± 5.6 | −12.4 | 7.9* ± 0.7 | −23.1 | 6.8 ± 0.3 | N.S. +1.5 |
| Compound A | 100 mg | 0.80** ± 0.08 | −42.9 | 109.1 ± 8.1 | N.S. −15.7 | 101.6 ± 7.1 | N.S. −14.7 | 7.5* ± 1.1 | −26.7 | 6.7 ± 0.2 | N.S. −0.3 |

N.S., not significant
* = p < 0.05; ** = p < 0.01 compared with vehicle treated control using Student's two-tailed t test.

EXAMPLE 42

Effect of Compound A on the impregnated sponqeqranuloma test in the rat.

Animals — AHH/R female rats (PVG derived) with an initial weight range of 120]140 g. were used.

Materials — Sponge preparation. Pellets (6.5 mm diameter) were punched from cellulose sponge cloth ("Wettex") and 0.1 ml. of a suspension containing 0.5 mg.ml$^{-1}$ of heat killed M. tuberculosis (human strains C, DT and PN) in sterile saline was applied to each pellet. The pellets were dried, weighed and autoclaved.

Method —Rats were randomly divided into groups of five and daily dosing with test compounds was commenced. After the fifth dose the rats were anaesthetised with Sagatal (45 mg.kg.$^{-1}$ i.p.) the backs were shaved and two pellets were implanted subcutaneously (one each side) into each rat through a small dorsal midline incision. The incision was closed and the rats allowed to recover from the anaesthetic.

Seven days after implantation the rats were killed and the pellets were removed, dissected free of extraneous tissue and weighed. Each pellet was then placed in a 4 ml aliquot of distilled water, chopped with fine scissors and sonicated. After centrifugation the Na$^+$ and K$^+$ content of the supernatant was determined by flame photometry. In addition the adrenal and thumus glands from each rat were dissected out and weighed and the lower hind limbs were removed for measurement of tibial bone breaking strain. Body weights were also recorded throughout the test period.

Results — The results are given in the following table (Table VI).

Assessment of results

The mean ± SE for each of the parameters was calculated and differences from the control values were determined by Student's t test (2-tailed). Percentage reductions of granuloma weight, Na+ and K+ content and percentage changes of adrenal and thymus, weight and tibial breaking strain were determined.

We claim:

1. A compound selected from the group of phenyl derivatives of the formula:

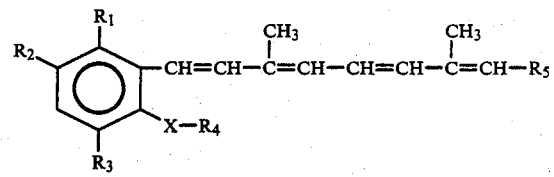

wherein $R_1$ is hydrogen, lower alkyl, chlorine, fluorine or trifluoromethyl; $R_2$ is chlorine, trifluoromethyl, lower alkyl, fluorine, hydroxy, loweralkoxy, trifluoromethylloweralkoxy, or hydrogen; $R_3$ is hydrogen, lower alkyl, chlorine, or fluorine; $R_4$ is an alkyl

TABLE VI

Effect of Compound A, etretinate and dexamethasone on the impreganted sponge granuloma test in rats

| Treatment | Dose mg.kg$^{-1}$ | No. 1. of rats | % reduction of granuloma Wet weight | Na+ | k+ | % change in adrenal weight | thymus weight | tibial breaking strains | Body weight change (g) |
|---|---|---|---|---|---|---|---|---|---|
| Control | — | 8 | — | — | — | — | — | — | +9.6 ± 1.3 |
| Compound A | 15 p.o | 5 | 15.1** | 14.5** | −6.9** | +17.6** | −4.4 | −4.0 | +7.2 ± 0.74 |
|  | 45 p.o | 5 | 10.8 | 11 | 0.8 | +29.0** | +14.3 | −1.12 | +11.4 ± 0.98 |
| Etretinate | 15 p.o | 4 | 2.7 | 5.9 | −3.9 | +22.9** | +15.2 | −4.6 | +13.3 ± 2.6 |
| Dexamethasone | 0.5 sc | 5 | 65.5*** | 51.2*** | 75.2*** | −49.5*** | −79*** | −11.5* | −10.2 ± 1.59 |

*p = <0.05; p = <0.02; *p = <0.01
/Comment 2 control rats and 1 etretinate treated rat died under anaesthesia.

Animals — Male Lewis rats from Charles River were used for these experiments.

Materials — Heat-killed, dessicated *Mycobacteriam butyricum*.

Method — Adjuvant arthritis was induced by the injection of 0.1 ml of adjuvant [a suspension of heat-killed, dessicated *Mycobacterium butyricum*, 0.5% CW/V) in heavy mineral oil containing 0.2% digitonin] into the base of the tail. The arthritis was allowed to develop for 21 days and then the volume of both hind paws were measured using a mercury plethysmograph. The rats were divided into groups of 8 with equal mean paw volumes and then the rats were treated with Compound A, indomethacin (as a control drug), or vehicle for 7 days at the end of the treatment period, the volumes of both hind paws were again measured to assess antiinflammatory effects. Body weight changes were also followed and, at the end of the experiment, plasma was collected for determination of plasma fibrinogen (Exner et. al., Amer. J. Clin. Path, 71: 521-527).

Results: The results are given in the following Table (Table VII).

group having a straight chain length of 4 to 9 carbon atoms; X is —O—; $R_5$ is $COOR_9$; and $R_9$ is hydrogen or lower alkyl; and pharmaceutically acceptable salts thereof.

2. The compound of claim 1 wherein $R_1$ is chlorine or fluorine.

3. The compound of claim 2 wherein $R_2$ and $R_3$ are hydrogen.

4. The compound of claim 3 wherein said phenyl derivative is 9-[2-chloro-6-(nonyloxy)phenyl]-3,7-dimethyl-2,4,6,8-nonatetraenoic acid.

5. The compound of claim 3 wherein said phenyl derivative is (all-E)-9-[2-fluoro-6-(nonyloxy)phenyl]-3,7-dimethyl-2,4,6,8-nonatetraenoic acid.

6. The compound of claim 1 wherein $R_1$ is trifluoromethyl.

7. The compound of claim 6 wherein $R_2$ and $R_3$ are hydrogen.

8. The compound of claim 7 wherein said compound is (all-E)-9-[2-(trifluoromethyl)-6-(nonyloxy)phenyl]-3,7-dimethyl-2,4,6,8-nonatetraenoic acid.

9. The compound of claim 1 wherein $R_2$ is lower alkoxyl.

TABLE VII

EFFECT ON THE COURSE OF ESTABLISHED ADJUVANT ARTHRITIS[a]

| Group | Treatment[b] | Dose (mg/kg) | Change in Paw[c] Volume (ml) | Plasma Fibrinogen (mg/dl) | Change in Body[c] Weight (g) |
|---|---|---|---|---|---|
| Arthritic(10)[b] | Vehicle | — | +0.53 ± 0.08 | 1773 ± 30 | 7.5 ± 1.2 |
| Arthritic(10) | Compound A | 100 | −0.96 ± 0.10* | 874 ± 57* | 5.2 ± 2.1 |
| Arthritic(10) | Indomethacin | 1 | −1.22 ± 0.15* | 978 ± 100* | 25.6 ± 3.1* |

[a]Means ± S.E. are reported.
[b]Drugs were administered once a day for 7 days by intubation starting on day 22 after induction of the arthritis. Tween 80 was used as vehicle.
[c]Change in paw volume/body weight equals paw volume/body weight on day 28 minus paw volume/body weight on day 22. Since adjuvant was injected into base of tail, change in paw volume is combined value for both hind paws.
[d]Number of animals per group.
*Significantly different from value for vehicle-treated arthritic animals (Student's t-test, p < 0.05).

10. The compound of claim 9 wherein $R_1$ and $R_3$ are hydrogen.

11. The compound of claim 10 wherein said phenyl derivative is 3,7-dimethyl-9-(5-methoxy-2-nonyloxylphenyl)2,4,6,8-nonatetraenoic acid.

12. The compound of claim 12 wherein $R_1$, $R_2$, and $R_3$ are hydrogen.

13. The compound of claim 12 wherein said phenyl derivative is 3,7-dimethyl-9-[2-(octyloxy)phenyl]2,4,6,8-nonatetraenoic acid.

14. The compound of claim 12 wherein said phenyl derivative is 9-[2-(nonyloxy)phenyl]-3,7-dimethyl-2,4,6,8-nonatetraenoic acid.

15. The compound of claim 12 wherein said phenyl derivative is 3,7-dimethyl-9-[2-(2,2-dimethyl-octyl)oxy]2,4,6,8-nonatetraenoic acid.

16. The compound of claim 12 wherein said phenyl derivative is 9-[2-(nonyloxylphenyl]-3,7-dimethyl-2,4,6,8-nonatetraenoic acid ethyl ester.

17. The compound of claim 12 wherein said compound is (all-E)-9-[2-(hexyloxy)phenyl 7-dimethyl-2,4,6,8-nonatetraenoic acid.

18. The compound of claim 1 wherein $R_2$ is hydroxy.

19. The compound of claim 18 wherein $R_1$ and $R_3$ are hydrogen.

20. The compound of claim 12 wherein said compound is (all-E)-9-[5-hydroxy-2-(nonyloxy)phenyl]-3.7-dimethyl-2,4,6,8-nonatetraenoic acid.

21. The compound of claim 1 wherein $R_2$ is trifluoromethylloweralkoxy.

22. The compound of claim 21 wherein $R_1$ and $R_3$ are hydrogen.

23. The compound of claim 22 wherein said compound is (all-E)-9-[2-(nonyloxy)-5-(2,2,2-trifluoroethoxy)phenyl]-3,7-dimethyl-2,4,6,8-nonatetraenoic acid.

* * * * *

UNITED STATES PATENT AND TRADEMARK OFFICE
CERTIFICATE OF CORRECTION

PATENT NO. : 4,883,614

DATED : November 28, 1989

INVENTOR(S) : AIG ET AL.

It is certified that error appears in the above-identified patent and that said Letters Patent is hereby corrected as shown below:

Column 35, line 7, "12" should be: 1

Column 36, line 5, "---phenyl 7-dimethyl -2,4,6---"
should be ---phenyl]-3,7-dimethyl-2,4,6,---

Column 36, line 10, "claim 12" should be: claim 19.

Signed and Sealed this

Seventeenth Day of September, 1991

Attest:

HARRY F. MANBECK, JR.

*Attesting Officer*  *Commissioner of Patents and Trademarks*